(12) United States Patent
Erickson et al.

(10) Patent No.: US 11,530,379 B2
(45) Date of Patent: Dec. 20, 2022

(54) DEVICES AND METHODS FOR INOCULATING A TARGET

(71) Applicant: STRATIX LABS CORPORATION, St. Paul, MN (US)

(72) Inventors: Joshua Erickson, Blaine, MN (US); Mark Mulvahill, St. Louis Park, MN (US); Maya Burroughs, St. Paul, MN (US)

(73) Assignee: STRATIX LABS CORPORATION, St. Paul, MN (US)

( * ) Notice: Subject to any disclaimer, the term of this patent is extended or adjusted under 35 U.S.C. 154(b) by 0 days.

(21) Appl. No.: 17/379,521

(22) Filed: Jul. 19, 2021

(65) Prior Publication Data

US 2022/0017848 A1 Jan. 20, 2022

Related U.S. Application Data

(60) Provisional application No. 63/053,800, filed on Jul. 20, 2020, provisional application No. 63/061,784, filed on Aug. 5, 2020, provisional application No. 63/138,636, filed on Jan. 18, 2021.

(51) Int. Cl.
| | | |
|---|---|---|
| *C12M 3/00* | (2006.01) | |
| *C12N 1/00* | (2006.01) | |
| *C12M 1/30* | (2006.01) | |
| *C12M 1/00* | (2006.01) | |
| *C12N 1/20* | (2006.01) | |

(52) U.S. Cl.
CPC ............ *C12M 33/02* (2013.01); *C12M 23/38* (2013.01); *C12N 1/20* (2013.01)

(58) Field of Classification Search
CPC .......... C12M 33/02; C12M 23/38; C12N 1/20
See application file for complete search history.

(56) References Cited

U.S. PATENT DOCUMENTS

| | | |
|---|---|---|
| 3,450,129 A | 6/1969 | Avery et al. |
| 3,671,400 A | 6/1972 | Cekoric, Jr. et al. |
| 3,843,456 A | 10/1974 | Haden et al. |
| 4,175,008 A | 11/1979 | White |
| 4,311,792 A | 1/1982 | Avery |

(Continued)

FOREIGN PATENT DOCUMENTS

WO 9715331 A1 5/1997

OTHER PUBLICATIONS

International Search Report and Written Opinion dated Nov. 24, 2021 for International Application No. PCT/US2021/042213.

(Continued)

*Primary Examiner* — Nathan A Bowers
(74) *Attorney, Agent, or Firm* — Seager, Tufte & Wickhem LLP

(57) ABSTRACT

Inoculating systems/devices, methods for inoculating a target, and coating methods are disclosed. An example inoculating system may include an inoculating member having a transfer region and a handle region. A pre-determined quantity of viable microorganisms may be disposed on the transfer region. The inoculating member may be configured to transfer the pre-determined quantity of viable microorganisms to a target during an inoculation operation without having to rehydrate the pre-determined quantity of viable microorganisms prior to the inoculating operation.

28 Claims, 9 Drawing Sheets

(56) References Cited

U.S. PATENT DOCUMENTS

| | | | |
|---|---|---|---|
| 4,353,868 A | 10/1982 | Joslin et al. | |
| 4,615,823 A | 10/1986 | Tokuyama et al. | |
| 4,687,746 A * | 8/1987 | Rosenberg | C12M 33/02 |
| | | | 435/309.3 |
| 4,749,655 A | 6/1988 | Monthony et al. | |
| 4,978,504 A | 12/1990 | Nason | |
| 5,078,968 A | 1/1992 | Nason | |
| 5,114,003 A | 5/1992 | Jackisch et al. | |
| 5,155,039 A | 10/1992 | Chrisope et al. | |
| 5,238,649 A | 8/1993 | Nason | |
| 5,266,266 A | 11/1993 | Nason | |
| 5,279,964 A | 1/1994 | Chrisope | |
| 5,733,777 A | 3/1998 | Dudney | |
| 5,856,172 A | 1/1999 | Greenwood et al. | |
| 5,879,635 A | 3/1999 | Nason | |
| 7,186,502 B2 | 3/2007 | Vesey | |
| 7,374,904 B2 | 5/2008 | Vesey et al. | |
| 7,645,608 B2 | 1/2010 | Greene | |
| D655,017 S | 2/2012 | Mosier et al. | |
| D681,230 S | 4/2013 | Mosier et al. | |
| 8,475,404 B2 | 7/2013 | Foshee et al. | |
| 8,821,436 B2 | 9/2014 | Mosier et al. | |
| 8,979,784 B2 | 3/2015 | Triva | |
| 9,011,358 B2 | 4/2015 | Triva | |
| 9,173,779 B2 | 11/2015 | Triva | |
| 9,428,788 B2 | 8/2016 | Triva | |
| D769,444 S | 10/2016 | Mosier et al. | |
| 9,504,452 B2 | 11/2016 | Triva | |
| 10,092,275 B2 | 10/2018 | Triva | |
| 10,327,741 B2 | 6/2019 | Triva | |
| 10,610,343 B2 | 4/2020 | Stroud | |
| 2006/0040340 A1 | 2/2006 | Greene | |
| 2007/0269886 A1* | 11/2007 | Qian | C12N 5/0606 |
| | | | 435/366 |
| 2010/0261270 A1* | 10/2010 | Peeters | C12N 5/0068 |
| | | | 435/378 |
| 2011/0087164 A1 | 4/2011 | Mosler et al. | |
| 2011/0174820 A1* | 7/2011 | Giles | B01L 3/508 |
| | | | 220/796 |
| 2014/0106445 A1 | 4/2014 | Triva | |
| 2015/0282916 A1 | 10/2015 | Stroud | |
| 2017/0071583 A1* | 3/2017 | McSherry | C12M 33/02 |
| 2017/0094986 A1 | 4/2017 | Brocheret et al. | |
| 2018/0280832 A1* | 10/2018 | Menon | B01D 63/087 |
| 2019/0144915 A1* | 5/2019 | Ward | C12M 23/38 |
| | | | 435/30 |
| 2020/0056219 A1* | 2/2020 | Young | C12M 23/04 |
| 2020/0299625 A1* | 9/2020 | Goral | C12M 23/20 |
| 2020/0354671 A1* | 11/2020 | Cross | A61L 27/52 |

OTHER PUBLICATIONS

Anonymous: "Instant Inoculator (TM) Qualitative QC microorganisms Brochure", XP055860989, Retrieved from the Internet: URL:https://stratixlabs.com/instant-inoculator [retrieved on Nov. 12, 2021] the whole document, Jun. 1, 2021.

Anonymous: "Instant Inoculator (TM) Qualitative QC Microorganisms Instructions for Use", pp. 1-2, XP055860985, Retrieved from the Internet: URL:https://stratixlabs.com/instant-inoculator [retrieved on Nov. 12, 2021] the whole document, Jun. 1, 2021.

* cited by examiner

DEVICES AND METHODS FOR INOCULATING A TARGET

CROSS-REFERENCE TO RELATED APPLICATIONS

This application claims priority to U.S. Provisional Application No. 63/053,800, filed on Jul. 20, 2020, claims priority to U.S. Provisional Application No. 63/061,784, filed on Aug. 5, 2020, and claims priority to U.S. Provisional Application No. 63/138,636, filed on Jan. 18, 2021, the entirety of which are incorporated herein by reference.

TECHNICAL FIELD

The present disclosure pertains to devices and methods for inoculating a target.

BACKGROUND

A number of devices have been developed for inoculating a target. Some of these devices include microbe transfer devices and/or the like. Of the known devices and methods, each has certain advantages and disadvantages. There is an ongoing need to provide alternative devices as well as alternative methods for manufacturing and using devices, for example devices for inoculating a target.

BRIEF SUMMARY

This disclosure provides design, material, manufacturing method, and use alternatives for inoculating devices. An inoculating system is disclosed. The inoculating system comprises: an inoculating member having a transfer region and a handle region; a pre-determined quantity of viable microorganisms disposed on the transfer region; and wherein the inoculating member is configured to transfer the pre-determined quantity of viable microorganisms to a target during an inoculation operation without having to rehydrate the pre-determined quantity of viable microorganisms prior to the inoculating operation.

Alternatively or additionally to any of the embodiments above, the pre-determined quantity of viable microorganisms includes dehydrated microorganisms.

Alternatively or additionally to any of the embodiments above, the pre-determined quantity of viable microorganisms includes lyophilized microorganisms.

Alternatively or additionally to any of the embodiments above, the pre-determined quantity of viable microorganisms includes freeze-dried microorganisms.

Alternatively or additionally to any of the embodiments above, the pre-determined quantity of viable microorganisms includes air-dried microorganisms.

Alternatively or additionally to any of the embodiments above, the pre-determined quantity of viable microorganisms is coated on the transfer region.

Alternatively or additionally to any of the embodiments above, the pre-determined quantity of viable microorganisms is arranged homogenously along the transfer region.

Alternatively or additionally to any of the embodiments above, the pre-determined quantity of viable microorganisms is arranged in a pattern along the transfer region.

Alternatively or additionally to any of the embodiments above, the pattern includes an array of microbial clusters.

Alternatively or additionally to any of the embodiments above, the pattern includes a plurality of clusters that each include one or more microbial cells that are designed to produce a distinct colony forming unit.

Alternatively or additionally to any of the embodiments above, the inoculating member is configured to transfer the pre-determined quantity of viable microorganisms to the target by pressing the transfer region against the target.

Alternatively or additionally to any of the embodiments above, the inoculating member is configured to transfer the pre-determined quantity of viable microorganisms to the target by stamping the transfer region against the target.

Alternatively or additionally to any of the embodiments above, the inoculating member is configured to transfer the pre-determined quantity of viable microorganisms to the target by brushing the transfer region along the target.

Alternatively or additionally to any of the embodiments above, the inoculating member is configured to transfer the pre-determined quantity of viable microorganisms to the target by pressing the transfer region along the target.

Alternatively or additionally to any of the embodiments above, the inoculating member is configured to transfer the pre-determined quantity of viable microorganisms to the target by spreading the transfer region along the target.

Alternatively or additionally to any of the embodiments above, the inoculating member is configured to transfer the pre-determined quantity of viable microorganisms to the target by contacting the transfer region to the target and then spreading the pre-determined quantity of viable microorganisms along the target.

Alternatively or additionally to any of the embodiments above, the transfer region is movable relative to the handle region.

Alternatively or additionally to any of the embodiments above, further comprising an actuator for moving the transfer region relative to the handle region.

Alternatively or additionally to any of the embodiments above, the actuator is configured to move the transfer region away from the handle region.

Alternatively or additionally to any of the embodiments above, further comprising a cap removably disposed over the transfer region.

Alternatively or additionally to any of the embodiments above, the target includes an agar plate.

Alternatively or additionally to any of the embodiments above, the target includes a liquid broth.

Alternatively or additionally to any of the embodiments above, the target has a water content of 5% or more.

Alternatively or additionally to any of the embodiments above, the target has a water content of 10% or more.

Alternatively or additionally to any of the embodiments above, the transfer region is substantially planar.

Alternatively or additionally to any of the embodiments above, the transfer region has a convex shape.

Alternatively or additionally to any of the embodiments above, the transfer region is non-porous.

Alternatively or additionally to any of the embodiments above, the transfer region includes a non-water soluble material.

Alternatively or additionally to any of the embodiments above, the transfer region includes polypropylene, polyethylene, polyethylene terephthalate, glycol modified polyethylene terephthalate, polystyrene, poly-lactic acid, acrylonitrile butadiene styrene, polyetheretherketone, polyoxymethylene, nylon, polycarbonate, polytetrafluoroethylene, or combinations thereof.

Alternatively or additionally to any of the embodiments above, the transfer region has a diameter of 1 mm or more.

Alternatively or additionally to any of the embodiments above, the transfer region has a diameter of 2 mm or more.

Alternatively or additionally to any of the embodiments above, the transfer region has a surface area of 0.75 $mm^2$ or more.

Alternatively or additionally to any of the embodiments above, the transfer region has a surface area of 3 $mm^2$ or more.

Alternatively or additionally to any of the embodiments above, the transfer region has a surface area of about 9000 $mm^2$ or less.

Alternatively or additionally to any of the embodiments above, a plurality of projections are disposed along the transfer region.

Alternatively or additionally to any of the embodiments above, the pre-determined quantity of viable microorganisms are disposed on one or more of the projections.

Alternatively or additionally to any of the embodiments above, the projections are arranged into an array along the transfer region.

Alternatively or additionally to any of the embodiments above, one or more of the projections include a convex surface.

Alternatively or additionally to any of the embodiments above, one or more of the projections include a planar surface.

Alternatively or additionally to any of the embodiments above, the transfer region includes 2 to 1,000 projections.

Alternatively or additionally to any of the embodiments above, the transfer region includes 2 to 100 projections.

Alternatively or additionally to any of the embodiments above, the transfer region includes 2 to 50 projections.

Alternatively or additionally to any of the embodiments above, one or more of the projections has a diameter of 1 mm or more.

Alternatively or additionally to any of the embodiments above, one or more of the projections has a diameter of 1 mm to 25 mm.

Alternatively or additionally to any of the embodiments above, one or more of the projections has a diameter of 1 mm to 10 mm.

Alternatively or additionally to any of the embodiments above, one or more of the projections has a diameter of 1 mm to 5 mm.

Alternatively or additionally to any of the embodiments above, one or more of the projections has a surface area of 0.5 $mm^2$ or more.

Alternatively or additionally to any of the embodiments above, one or more of the projections has a surface area of 0.5 $mm^2$ to 1,000 $mm^2$.

Alternatively or additionally to any of the embodiments above, one or more of the projections has a surface area of 0.5 $mm^2$ to 100 $mm^2$.

Alternatively or additionally to any of the embodiments above, one or more of the projections has a surface area of 0.5 $mm^2$ to 20 $mm^2$.

Alternatively or additionally to any of the embodiments above, the projections include a rounded peripheral surface.

Alternatively or additionally to any of the embodiments above, the projections include a blunt peripheral surface.

Alternatively or additionally to any of the embodiments above, the projections include an unsharp peripheral surface.

Alternatively or additionally to any of the embodiments above, the transfer region includes a rounded peripheral surface.

Alternatively or additionally to any of the embodiments above, the transfer region includes a blunt peripheral surface.

Alternatively or additionally to any of the embodiments above, the transfer region includes a unsharp peripheral surface.

Alternatively or additionally to any of the embodiments above, the inoculating member is disposable.

Alternatively or additionally to any of the embodiments above, the pre-determined quantity of microorganism includes bacteria.

Alternatively or additionally to any of the embodiments above, the pre-determined quantity of microorganism includes 1 to 1000 colony forming units of viable microorganisms.

Alternatively or additionally to any of the embodiments above, the pre-determined quantity of microorganism includes 1 to 100 colony forming units of viable microorganisms.

Alternatively or additionally to any of the embodiments above, the transfer region is configured to transfer 50% or more of the pre-determined quantity of viable microorganisms to the target.

Alternatively or additionally to any of the embodiments above, the transfer region is configured to transfer 75% or more of the pre-determined quantity of viable microorganisms to the target.

Alternatively or additionally to any of the embodiments above, the transfer region is configured to transfer 90% or more of the pre-determined quantity of viable microorganisms to the target.

Alternatively or additionally to any of the embodiments above, the transfer region has a transfer efficiency of 50% or more.

Alternatively or additionally to any of the embodiments above, the transfer region has a transfer efficiency of 75% or more.

Alternatively or additionally to any of the embodiments above, the transfer region has a transfer efficiency of 90% or more.

Alternatively or additionally to any of the embodiments above, the transfer region has a transfer efficacy of 50% or more.

Alternatively or additionally to any of the embodiments above, the transfer region has a transfer efficacy of 75% or more.

Alternatively or additionally to any of the embodiments above, the transfer region has a transfer efficacy of 90% or more.

Alternatively or additionally to any of the embodiments above, further comprising a package containing the inoculating member.

Alternatively or additionally to any of the embodiments above, the package includes a metal foil.

Alternatively or additionally to any of the embodiments above, the package includes a desiccant.

Alternatively or additionally to any of the embodiments above, the package includes an oxygen scavenger.

Alternatively or additionally to any of the embodiments above, the relative humidity inside of the package is 10% or more.

Alternatively or additionally to any of the embodiments above, the relative humidity inside of the package is 10-30%.

Alternatively or additionally to any of the embodiments above, the relative humidity inside of the package is 20-30%.

Alternatively or additionally to any of the embodiments above, the relative humidity inside of the package is 20% or more.

Alternatively or additionally to any of the embodiments above, the relative humidity inside of the package is 30% or more.

Alternatively or additionally to any of the embodiments above, the pre-determined quantity of microorganisms are room temperature stable.

Alternatively or additionally to any of the embodiments above, the pre-determined quantity of microorganisms are stable at a temperature of 20° C. or less.

Alternatively or additionally to any of the embodiments above, the pre-determined quantity of microorganisms are stable at a temperature of 4° C. or less.

Alternatively or additionally to any of the embodiments above, the pre-determined quantity of microorganisms have a viability of 50% or more after 30 days.

Alternatively or additionally to any of the embodiments above, the pre-determined quantity of microorganisms have a viability of 90% or more after 30 days.

Alternatively or additionally to any of the embodiments above, the pre-determined quantity of microorganisms have a viability of 50% or more at 20° C. for 90 days.

Alternatively or additionally to any of the embodiments above, the pre-determined quantity of microorganisms have a viability of 75% or more at 20° C. for 90 days.

Alternatively or additionally to any of the embodiments above, the pre-determined quantity of microorganisms have a viability of 90% or more at 20° C. for 90 days.

An inoculating system is disclosed. The inoculating system comprises: an inoculating member having a transfer region and a handle region; a pre-determined quantity of viable microorganisms disposed on the transfer region; and wherein the inoculating member is configured to transfer the pre-determined quantity of viable microorganisms to a target during an inoculation operation without having to conduct a spreading operation.

Alternatively or additionally to any of the embodiments above, the transfer region has a surface area of 200 mm$^2$ or greater.

Alternatively or additionally to any of the embodiments above, the target has a surface area of 200 mm$^2$ or greater.

An inoculating system is disclosed. The inoculating system comprises: an inoculating member having a transfer region; a pre-determined quantity of viable microorganisms disposed on the transfer region; and wherein the inoculating member is configured to transfer the pre-determined quantity of viable microorganisms to a target during an inoculation operation without having to rehydrate the pre-determined quantity of viable microorganisms prior to the inoculating operation.

Alternatively or additionally to any of the embodiments above, the inoculating member is configured to remain in contact with the target after transferring the pre-determined quantity of microorganisms to the target.

An inoculating system is disclosed. The inoculating system comprises: an inoculating member having a transfer region; a pre-determined quantity of viable microorganisms disposed on the transfer region; and wherein the inoculating member is configured to transfer the pre-determined quantity of viable microorganisms to a target during an inoculation operation without having to conduct a spreading operation.

Alternatively or additionally to any of the embodiments above, the transfer region has a surface area of 200 mm$^2$ or greater.

Alternatively or additionally to any of the embodiments above, the target has a surface area of 200 mm$^2$ or greater.

Alternatively or additionally to any of the embodiments above, the inoculating member is configured to remain in contact with the target after transferring the pre-determined quantity of microorganisms to the target.

A method for coating microorganisms onto a transfer device is disclosed. The method comprises: applying a coating solution onto a transfer region of a transfer device, wherein the coating solution comprises a plurality of microorganisms and a stabilizing mixture; and air-drying the coating solution.

Alternatively or additionally to any of the embodiments above, the stabilizing mixture includes a sugar.

Alternatively or additionally to any of the embodiments above, the stabilizing mixture includes a non-reducing sugar.

Alternatively or additionally to any of the embodiments above, the stabilizing mixture includes sucrose.

Alternatively or additionally to any of the embodiments above, the stabilizing mixture includes an antioxidant.

Alternatively or additionally to any of the embodiments above, the stabilizing mixture includes ascorbic acid.

Alternatively or additionally to any of the embodiments above, the stabilizing mixture includes a surfactant.

Alternatively or additionally to any of the embodiments above, the stabilizing mixture includes Triton X-100.

Alternatively or additionally to any of the embodiments above, the stabilizing mixture includes a nonionic surfactant.

Alternatively or additionally to any of the embodiments above, the stabilizing mixture includes an amino acid.

Alternatively or additionally to any of the embodiments above, the stabilizing mixture includes a protein.

Alternatively or additionally to any of the embodiments above, the stabilizing mixture includes a salt.

Alternatively or additionally to any of the embodiments above, the stabilizing mixture includes a polymer.

Alternatively or additionally to any of the embodiments above, the stabilizing mixture includes a buffer.

Alternatively or additionally to any of the embodiments above, the stabilizing mixture includes a phosphate buffer.

Alternatively or additionally to any of the embodiments above, the stabilizing mixture includes phosphate buffered saline.

Alternatively or additionally to any of the embodiments above, the stabilizing mixture includes tris(hydroxymethyl)aminomethane.

Alternatively or additionally to any of the embodiments above, the stabilizing mixture includes 2-[4-(2,4,4-trimethylpentan-2-yl)phenoxy]ethanol.

Alternatively or additionally to any of the embodiments above, the stabilizing mixture includes a growth nutrient.

Alternatively or additionally to any of the embodiments above, the stabilizing mixture includes a broth.

Alternatively or additionally to any of the embodiments above, the stabilizing mixture includes 0.1% to 15% of a sugar.

Alternatively or additionally to any of the embodiments above, the stabilizing mixture includes 0.01% to 5% of an antioxidant.

Alternatively or additionally to any of the embodiments above, the stabilizing mixture includes 0.001% to 2% of a surfactant.

Alternatively or additionally to any of the embodiments above, applying a coating solution onto a transfer region of a transfer device includes applying 1-100 microliters of the coating solution onto the transfer region.

Alternatively or additionally to any of the embodiments above, applying a coating solution onto a transfer region of a transfer device includes applying 5 microliters or less of the coating solution onto the transfer region.

Alternatively or additionally to any of the embodiments above, applying a coating solution onto a transfer region of a transfer device includes applying 1 microliter or less of the coating solution onto the transfer region.

Alternatively or additionally to any of the embodiments above, applying a coating solution onto a transfer region of a transfer device includes applying 1 nanoliter or less of the coating solution onto the transfer region.

Alternatively or additionally to any of the embodiments above, air-drying the coating solution includes air-drying the coating solution for 1-10 minutes.

Alternatively or additionally to any of the embodiments above, air-drying the coating solution includes air-drying the coating solution for 1-20 minutes.

Alternatively or additionally to any of the embodiments above, air-drying the coating solution includes air-drying the coating solution for 1-30 minutes.

Alternatively or additionally to any of the embodiments above, air-drying the coating solution includes air-drying the coating solution for 1-60 minutes.

Alternatively or additionally to any of the embodiments above, air-drying the coating solution includes air-drying the coating solution at room temperature.

Alternatively or additionally to any of the embodiments above, air-drying the coating solution includes air-drying the coating solution at 25° C. to 40° C.

Alternatively or additionally to any of the embodiments above, applying a coating solution onto a transfer region of a transfer device includes spreading the coating solution onto the transfer region with a spreading device.

Alternatively or additionally to any of the embodiments above, applying a coating solution onto a transfer region of a transfer device does not include spreading the coating solution onto the transfer region with a spreading device.

Alternatively or additionally to any of the embodiments above, applying a coating solution onto a transfer region of a transfer device includes arranging the coating solution in a homogeneous pattern along the transfer region.

Alternatively or additionally to any of the embodiments above, applying a coating solution onto a transfer region of a transfer device includes disposing the coating solution homogeneously along the transfer region.

Alternatively or additionally to any of the embodiments above, applying a coating solution onto a transfer region of a transfer device includes arranging the coating solution in a pattern along the transfer region.

Alternatively or additionally to any of the embodiments above, the pattern includes an array of microbial clusters.

Alternatively or additionally to any of the embodiments above, the pattern includes a plurality of clusters that each include one or more microbial cells that are designed to produce a distinct colony forming unit.

Alternatively or additionally to any of the embodiments above, further comprising disposing the transfer device into a package.

Alternatively or additionally to any of the embodiments above, the package includes a moisture barrier package.

Alternatively or additionally to any of the embodiments above, the package includes aluminum.

Alternatively or additionally to any of the embodiments above, the package includes a desiccant.

Alternatively or additionally to any of the embodiments above, the package includes an oxygen scavenger.

A device for inoculating a target without needing to rehydrate prior to an inoculation operation is disclosed. The device comprises: an inoculating member having a transfer region and a handle region; a pre-determined quantity of viable microorganisms disposed on the transfer region; wherein the inoculating member is configured to transfer the pre-determined quantity of viable microorganisms to a target by contacting the transfer region with the target; and a cover disposed over the transfer region.

An apparatus for inoculating a target with a quantity of microorganisms without needing to rehydrate the microorganisms prior to an inoculation operation is disclosed. The apparatus comprises: a transfer member having a transfer region and a handle region; a pre-determined quantity of viable microorganisms disposed on the transfer region; wherein the transfer member is configured to transfer the pre-determined quantity of viable microorganisms to a target by contacting the transfer region with the target; and a cover disposed over the transfer region.

A packaging assembly is disclosed. The packaging assembly comprises: a moisture barrier container configured to house an inoculation device having a pre-determined quantity of microorganisms coated thereon; a desiccant disposed in the moisture barrier container; an oxygen scavenger disposed in the moisture barrier container; wherein the moisture barrier container is configured to maintain a relative humidity of 10-30% within the moisture barrier container; and wherein the moisture barrier container is configured to have an oxygen content of 1% or less.

A modified atmosphere packaging assembly is disclosed. The modified atmosphere packaging assembly comprises: a moisture barrier container configured to house an inoculation device; wherein the inoculation device comprises an inoculating member having a transfer region and a handle region, a pre-determined quantity of viable microorganisms disposed on the transfer region, and wherein the inoculating member is configured to transfer the pre-determined quantity of viable microorganisms to a target during an inoculation operation without having to rehydrate the pre-determined quantity of viable microorganisms prior to the inoculating operation; and wherein the moisture barrier container is configured to have an oxygen content of 1% or less.

Alternatively or additionally to any of the embodiments above, the inoculation device is sealed in the moisture barrier container.

Alternatively or additionally to any of the embodiments above, further comprising a desiccant disposed in the moisture barrier container.

Alternatively or additionally to any of the embodiments above, further comprising an oxygen scavenger disposed in the moisture barrier container.

Alternatively or additionally to any of the embodiments above, further comprising a gas disposed within the moisture barrier container.

Alternatively or additionally to any of the embodiments above, the gas includes nitrogen.

A modified atmosphere packaging assembly is disclosed. The modified atmosphere packaging assembly comprises: a moisture barrier container configured to house an inoculation device; wherein the inoculation device comprises an inoculating member having a transfer region and a handle region, a pre-determined quantity of viable microorganisms disposed on the transfer region, and wherein the inoculating member is configured to transfer the viable microorganism to a target during an inoculation operation without having to conduct a spreading operation; and wherein the moisture barrier container is configured to have an oxygen content of 1% or less.

Alternatively or additionally to any of the embodiments above, the inoculation device is sealed in the moisture barrier container.

Alternatively or additionally to any of the embodiments above, further comprising a desiccant disposed in the moisture barrier container.

Alternatively or additionally to any of the embodiments above, further comprising an oxygen scavenger disposed in the moisture barrier container.

Alternatively or additionally to any of the embodiments above, further comprising a gas disposed within the moisture barrier container.

Alternatively or additionally to any of the embodiments above, the gas includes nitrogen.

An inoculating system is disclosed. The inoculating system comprises: an inoculating member having a transfer region and a handle region; wherein a plurality of projections are disposed along the transfer region; a pre-determined quantity of viable microorganisms disposed on one or more of the projections; and wherein the inoculating member is configured to transfer the pre-determined quantity of viable microorganisms to a target during an inoculation operation.

Alternatively or additionally to any of the embodiments above, the projections are arranged as an array along the transfer region.

Alternatively or additionally to any of the embodiments above, the transfer region is non-porous.

Alternatively or additionally to any of the embodiments above, the transfer region includes a non-water soluble material.

Alternatively or additionally to any of the embodiments above, the transfer region has a convex surface.

Alternatively or additionally to any of the embodiments above, one or more of the projections have a convex surface.

Alternatively or additionally to any of the embodiments above, the transfer region includes 2 to 1,000 projections.

Alternatively or additionally to any of the embodiments above, the transfer region includes 2 to 100 projections.

Alternatively or additionally to any of the embodiments above, the transfer region includes 2 to 50 projections.

Alternatively or additionally to any of the embodiments above, one or more of the projections has a diameter of 1 mm or more.

Alternatively or additionally to any of the embodiments above, one or more of the projections has a diameter of 1 mm to 25 mm.

Alternatively or additionally to any of the embodiments above, one or more of the projections has a diameter of 1 mm to 10 mm.

Alternatively or additionally to any of the embodiments above, one or more of the projections has a diameter of 1 mm to 5 mm.

Alternatively or additionally to any of the embodiments above, one or more of the projections has a surface area of $0.5$ mm$^2$ or more.

Alternatively or additionally to any of the embodiments above, one or more of the projections has a surface area of $0.5$ mm$^2$ to $1,000$ mm$^2$.

Alternatively or additionally to any of the embodiments above, one or more of the projections has a surface area of $0.5$ mm$^2$ to $100$ mm$^2$.

Alternatively or additionally to any of the embodiments above, one or more of the projections has a surface area of $0.5$ mm$^2$ to $20$ mm$^2$.

A method for transferring a pre-determined quantity of viable microorganisms to a target is disclosed. The method comprises: opening a package containing an inoculating device, the inoculating device including a handle region, a transfer region, a pre-determined quantity of viable microorganisms disposed along the transfer region, and a cap disposed over the inoculating device; removing the inoculating device from the package; removing the cap from the transfer region; and contacting the transfer region with a target.

A method for transferring a pre-determined quantity of viable microorganisms to a target is disclosed. The method comprises: removing an inoculating device from a sealed package, the inoculating device including a handle region, a transfer region, a pre-determined quantity of viable microorganisms disposed along the transfer region, and a cap disposed over the inoculating device; removing the cap from the transfer region; and contacting the transfer region with a target without having to rehydrate the pre-determined quantity of viable microorganisms in a separate step.

A method for inoculating a target is disclosed. The method comprises: removing an inoculating device from a sealed package, the inoculating device including a handle region, a transfer region, a pre-determined quantity of viable microorganisms disposed along the transfer region, and a cap disposed over the inoculating device; removing the cap from the transfer region; contacting the transfer region with a target; maintaining contact for a contact time wherein one or more viable microorganisms are transferred from the transfer region to the target without conducting a spreading operation; removing the transfer region from contact with the target; incubating the target for an incubation time; and observing an indication of growth.

Alternatively or additionally to any of the embodiments above, one or more viable microorganisms are hydrated by the target at substantially the same time as when they are transferred.

Alternatively or additionally to any of the embodiments above, observing an indication of growth includes a qualitative assessment.

Alternatively or additionally to any of the embodiments above, observing an indication of growth includes a quantitative assessment.

Alternatively or additionally to any of the embodiments above, observing an indication of growth includes evaluating viability.

Alternatively or additionally to any of the embodiments above, observing an indication of growth includes evaluating fluorescence.

Alternatively or additionally to any of the embodiments above, observing an indication of growth includes detection of a fluorescent microorganism.

Alternatively or additionally to any of the embodiments above, observing an indication of growth includes evaluating optical density or absorbance.

Alternatively or additionally to any of the embodiments above, observing an indication of growth includes evaluating pH.

Alternatively or additionally to any of the embodiments above, observing an indication of growth includes evaluating a change in color.

Alternatively or additionally to any of the embodiments above, observing an indication of growth includes enumeration of colony forming units.

Alternatively or additionally to any of the embodiments above, observing an indication of growth includes manual colony counting.

Alternatively or additionally to any of the embodiments above, observing an indication of growth includes automated colony counting.

Alternatively or additionally to any of the embodiments above, observing an indication of growth includes enumeration of 1-1,000 colony forming units.

Alternatively or additionally to any of the embodiments above, observing an indication of growth includes enumeration of 1-100 colony forming units.

Alternatively or additionally to any of the embodiments above, observing an indication of growth includes visually observing a predetermined pattern on the culture medium.

Alternatively or additionally to any of the embodiments above, the target is a liquid broth.

Alternatively or additionally to any of the embodiments above, the target is a solid agar.

Alternatively or additionally to any of the embodiments above, the microbial transfer efficacy is greater than 50%.

Alternatively or additionally to any of the embodiments above, the microbial transfer efficacy is greater than 75%.

Alternatively or additionally to any of the embodiments above, the microbial transfer efficacy is greater than 90%.

Alternatively or additionally to any of the embodiments above, the pre-determined quantity of microorganisms is between 1-1,000 colony forming units.

Alternatively or additionally to any of the embodiments above, the predetermined quantity of microorganisms is between 1-100 colony forming units.

Alternatively or additionally to any of the embodiments above, 1 to 1,000 colony forming units of viable microorganisms are transferred from the device to the target.

Alternatively or additionally to any of the embodiments above, 1 to 100 colony forming units of viable microorganisms are transferred from the device to the target.

Alternatively or additionally to any of the embodiments above, contacting the device to the culture medium comprises pressing the transfer region against the culture medium.

Alternatively or additionally to any of the embodiments above, contacting the device to the culture medium comprises stamping the transfer region against the culture medium.

Alternatively or additionally to any of the embodiments above, contacting the device to the culture medium comprises spreading the transfer region along the culture medium.

Alternatively or additionally to any of the embodiments above, contacting the device to the culture medium comprises brushing the transfer region along the culture medium.

Alternatively or additionally to any of the embodiments above, the contact time is less than 30 seconds.

Alternatively or additionally to any of the embodiments above, the contact time is less than 15 seconds.

Alternatively or additionally to any of the embodiments above, the contact time is less than 10 seconds.

Alternatively or additionally to any of the embodiments above, the contact time is less than 5 seconds.

Alternatively or additionally to any of the embodiments above, the contact time is less than 1 second.

Alternatively or additionally to any of the embodiments above, after the incubation time at least one colony forming unit is distinct and countable.

Alternatively or additionally to any of the embodiments above, after the incubation time all colony forming units are distinct and countable.

A method for inoculating a target is disclosed. The method comprises: removing an inoculating device from a sealed package, the inoculating device including a handle region, a transfer region, a pre-determined quantity of viable microorganisms disposed along the transfer region, and a cap disposed over the inoculating device; removing the cap from the transfer region; contacting the transfer region with a target without having to rehydrate the pre-determined quantity of viable microorganisms prior to the inoculating operation; maintaining contact for a contact time wherein one or more viable microorganisms are transferred from the transfer region to the target; removing the transfer region from contact with the target; incubating the target for an incubation time; and observing an indication of growth.

Alternatively or additionally to any of the embodiments above, one or more viable microorganisms are hydrated by the target at substantially the same time as when they are transferred.

Alternatively or additionally to any of the embodiments above, the inoculating device may not require or include a cap disposed over the inoculating device.

Alternatively or additionally to any of the embodiments above, a method for inoculating a target may not require or include removing a cap from the transfer region of the inoculating device.

Alternatively or additionally to any of the embodiments above, observing an indication of growth includes a qualitative assessment.

Alternatively or additionally to any of the embodiments above, observing an indication of growth includes a quantitative assessment.

Alternatively or additionally to any of the embodiments above, observing an indication of growth includes evaluating viability.

Alternatively or additionally to any of the embodiments above, observing an indication of growth includes evaluating fluorescence.

Alternatively or additionally to any of the embodiments above, observing an indication of growth includes detection of a fluorescent microorganism.

Alternatively or additionally to any of the embodiments above, observing an indication of growth includes evaluating optical density or absorbance.

Alternatively or additionally to any of the embodiments above, observing an indication of growth includes evaluating pH.

Alternatively or additionally to any of the embodiments above, observing an indication of growth includes evaluating a change in color.

Alternatively or additionally to any of the embodiments above, observing an indication of growth includes enumeration of colony forming units.

Alternatively or additionally to any of the embodiments above, observing an indication of growth includes manual colony counting.

Alternatively or additionally to any of the embodiments above, observing an indication of growth includes automated colony counting.

Alternatively or additionally to any of the embodiments above, observing an indication of growth includes enumeration of 1-1,000 colony forming units.

Alternatively or additionally to any of the embodiments above, observing an indication of growth includes enumeration of 1-100 colony forming units.

Alternatively or additionally to any of the embodiments above, observing an indication of growth includes visually observing a predetermined pattern on the culture medium.

Alternatively or additionally to any of the embodiments above, the target is a liquid broth.

Alternatively or additionally to any of the embodiments above, the target is a solid agar.

Alternatively or additionally to any of the embodiments above, the microbial transfer efficacy is greater than 50%.

Alternatively or additionally to any of the embodiments above, the microbial transfer efficacy is greater than 75%.

Alternatively or additionally to any of the embodiments above, the microbial transfer efficacy is greater than 90%.

Alternatively or additionally to any of the embodiments above, the pre-determined quantity of microorganisms is between 1-1,000 colony forming units.

Alternatively or additionally to any of the embodiments above, the predetermined quantity of microorganisms is between 1-100 colony forming units.

Alternatively or additionally to any of the embodiments above, 1 to 1,000 colony forming units of viable microorganisms are transferred from the device to the target.

Alternatively or additionally to any of the embodiments above, 1 to 100 colony forming units of viable microorganisms are transferred from the device to the target.

Alternatively or additionally to any of the embodiments above, contacting the device to the culture medium comprises pressing the transfer region against the culture medium.

Alternatively or additionally to any of the embodiments above, contacting the device to the culture medium comprises stamping the transfer region against the culture medium.

Alternatively or additionally to any of the embodiments above, contacting the device to the culture medium comprises spreading the transfer region along the culture medium.

Alternatively or additionally to any of the embodiments above, contacting the device to the culture medium comprises brushing the transfer region along the culture medium.

Alternatively or additionally to any of the embodiments above, the contact time is less than 30 seconds.

Alternatively or additionally to any of the embodiments above, the contact time is less than 15 seconds.

Alternatively or additionally to any of the embodiments above, the contact time is less than 10 seconds.

Alternatively or additionally to any of the embodiments above, the contact time is less than 5 seconds.

Alternatively or additionally to any of the embodiments above, the contact time is less than 1 second.

Alternatively or additionally to any of the embodiments above, after the incubation time at least one colony forming unit is distinct and countable.

Alternatively or additionally to any of the embodiments above, after the incubation time all colony forming units are distinct and countable.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
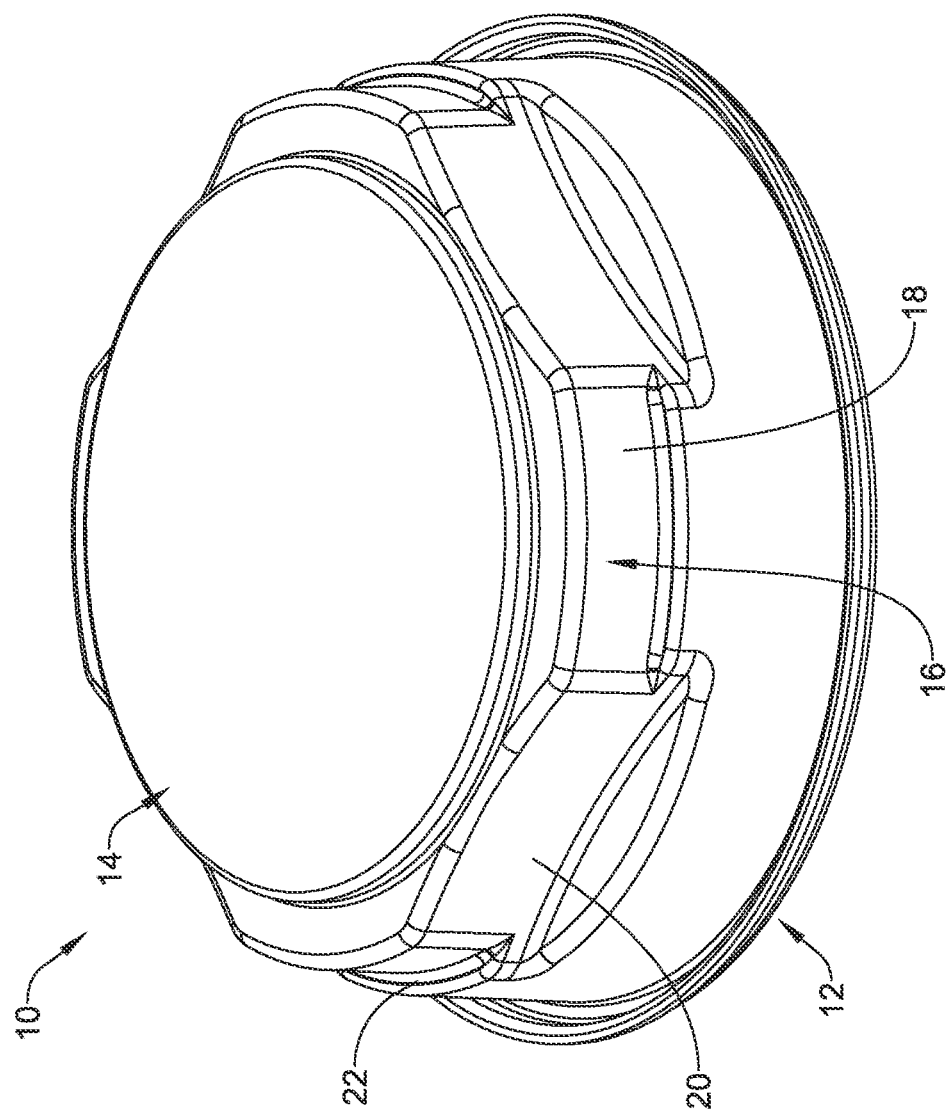
FIG. 1 is a perspective view of an example inoculating device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Precise and controlled inoculation and/or transfer of microorganisms to a target is useful in a number of different settings. For example, in a number of laboratory settings it may be desirable for control and/or validation testing that demonstrates the viability of certain targets. In some instances, the target may include an agar plate. Example testing processes may include growth promotion testing, environmental testing, and/or the like. In other instances, it may be desirable to transfer or utilize a precise number of microorganisms. Disclosed herein are devices and methods for inoculating and/or transferring microorganisms to a target.

FIG. 1 is a perspective view of an example inoculation device 10. The device 10 may have a number of uses such as for inoculating a target/substrate. The target (not shown in FIG. 1) may be a solid target (e.g., an agar plate) or a liquid target or media. The device 10 may include a base or handle region 12 and a transfer region 14. The handle region 12 may be configured so that a user can grip or hold the device 10 during use. The transfer region 14 may have a pre-determined quantity of viable microorganisms disposed thereon. The microorganisms may be disposed/coated onto the transfer region 14 and dried/dehydrated in a manner that maintains the viability of the microorganism and that allows for transfer of the microorganisms in a relatively simple manner that does not require rehydration of the microorganisms prior to an inoculating/transfer process (e.g., prior to contacting the target). Thus, the use of the device 10 does not require any additional rehydration steps (e.g., where the microorganisms are rehydrated) in order to efficiently transfer the microorganisms to the target in a relatively simple, straightforward manner such as merely contacting the transfer region 14 with the target.

While in some instances it may be desirable to utilize a pre-determined quantity of microorganisms, in other instances knowing the quantity of microorganisms may not be required. Therefore, in the examples disclosed herein, either a pre-determined quantity of microorganisms may be utilized or a quantity of microorganisms that is not precisely known may be utilized.

The transfer region 14 may have a suitable shape, size, and material composition that aids in facilitating the transfer of microorganisms disposed thereon to a target. For example, the transfer region 14 may have a substantially round or rounded shape as depicted in FIG. 1. Other shapes such as regular shapes, irregular shapes, and/or polygonal shapes including regular polygons and irregular polygons (e.g., having 1, 2, 3, 4, 5, 6, 7, 8, 9, 10, or more sides) may be utilized for the transfer region 14. In some instances, the transfer region 14 may be convex or otherwise bow/arc away from the handle region 12. In other instances, the transfer region 14 may be substantially planar. In at least some instances, the sides or peripheral surfaces of the transfer region 14 may be rounded, blunt, unsharp, or the like.

In some instances, the transfer region 14 may be formed from or otherwise include a suitable material such as metal, steel, glass, plastic/polymer, and/or the like. Some examples of suitable polymers may include polypropylene, polyethylene, polyethylene terephthalate, glycol modified polyethylene terephthalate, polystyrene, poly-lactic acid, acrylonitrile butadiene styrene, polyetheretherketone, polyoxymethylene, nylon, polycarbonate, polytetrafluoroethylene, combinations thereof, and/or the like. In some of these and in other instances, the transfer region 14 may be formed from a non-water soluble material. In some of these and in other instances, the transfer region 14 may be formed from a substantially non-porous material and/or otherwise be considered to be non-porous. The device 10 may be manufactured using a suitable process such as a thermoforming, injection molding, molding, casting, and/or the like.

The transfer region 14 (e.g., when having a round or rounded shape) may have a size or diameter of about 10 mm or more, or about 20 mm or more, or about 30 mm or more, or about 10-200 mm. The surface area of the transfer region 14 may be about 15,000 $mm^2$ or less, or about 10,000 $mm^2$ or less, or about 9,000 $mm^2$ or less, or about 5,000 $mm^2$ or less, or about 10 $mm^2$ to 10,000 $mm^2$, or about 0.75 $mm^2$ or more, or about 3 $mm^2$ or more, or at least 200 $mm^2$ (e.g., at least 250 $mm^2$, at least 300 $mm^2$, at least 350 $mm^2$, at least 400 $mm^2$, at least 450 $mm^2$, at least 500 $mm^2$, at least 550 $mm^2$, at least 600 $mm^2$, at least 650 $mm^2$, at least 700 $mm^2$, at least 750 $mm^2$, at least 800 $mm^2$, at least 850 $mm^2$, at least 900 $mm^2$, at least 950 $mm^2$, or at least 1,000 $mm^2$). The dimensions of the transfer region 14 may be selected in order to accommodate a particular target (e.g., the transfer region 14 may be sized for use with an agar plate). In addition, the size/dimensions may be selected so that the transfer region 14 can be brought into contact with target and allow for spreading action with on the target. For example, in some instances the target may have a surface area of at least 200 $mm^2$ (e.g., at least 250 $mm^2$, at least 300 $mm^2$, at least 350 $mm^2$, at least 400 $mm^2$, at least 450 $mm^2$, at least 500 $mm^2$, at least 550 $mm^2$, at least 600 $mm^2$, at least 650 $mm^2$, at least 700 $mm^2$, at least 750 $mm^2$, at least 800 $mm^2$, at least 850 $mm^2$, at least 900 $mm^2$, at least 950 $mm^2$, or at least 1,000 $mm^2$).

The device 10 may also include a cap receiving region 16. The cap receiving region 16 may include a generally cylindrical section 18. One or more spacer sections 20 may be defined about the cylindrical section 18. The spacer sections 20 may be disposed or generally be oriented radially inward of the cylindrical section 18. In some instances, the spacer sections 20 may be or resemble cutouts in the cylindrical section 18. The orientation of the spacer sections 20 may allow for some amount of air flow or venting along the cap receiving region 16. The cap receiving region 16 may also include a recessed or grooved region 22 that may be configured to receive a cap as described in more detail herein.

In use, the device 10 may be brought into contact with the target to transfer the microorganisms. When the device 10 is disposed within a package, the process may include opening the package and removing the device 10 from the package. When the target is a solid target, this may include bringing the transfer region 14 into contact with the target. In some instances, bringing the transfer region 14 into contact with the target may include pressing the transfer region 14 onto/against/along the target, stamping the transfer region 14 onto/against/along the target, brushing the transfer region 14 onto/against/along the target, spreading the transfer region 14 onto/against/along the target, imprinting the transfer region 14 onto the target, contacting the transfer region 14 with the target and then spreading the pre-determined quantity of viable microorganisms along the target, combinations thereof, and/or the like. In some instances, after being brought into contact with the target to transfer the microorganisms, the transfer region 14 may be configured to remain in contact with the target for a contact time (e.g., about 30 seconds or less, or about 15 seconds or less, or about 10 seconds or less, or about 5 seconds or less, or about 1 second or less). In some of these and in other instances, the transfer region 14 may be configured to remain in contact indefinitely. In some instances, a spreading action may be utilized after contacting the transfer region 14 with the target. In other instances, a spreading action is not required (e.g., the transfer region 14 is configured to transfer the pre-determined quantity of viable microorganisms to a target during an inoculation operation without having to conduct a spreading operation). If desired, the transfer region 14 may be removed from contact with the target.

The target may be incubated for a suitable incubation time. After the suitable incubation time, a user may observe the target for an indication of growth. Observing the target for an indication of growth may include a qualitative assessment, a quantitative assessment, evaluating viability, evaluating fluorescence, detection of a fluorescent microorganism, evaluating pH, evaluating a change in color, enumeration of colony forming units, manual colony counting, automated colony counting, enumeration of 1-100 colony forming units, visually observing a predetermined pattern on the culture medium, combinations thereof, and/or the like.

When the transfer region 14 is brought into contact with the target, the microorganisms may essentially simultaneously become at least partially rehydrated due to the water content of the target itself and transfer the microorganisms to the target. For example, the target may have a water content of about 5% or more, or about 10% or more. Because the microorganisms are able to become sufficiently hydrated/transferred by simply contacting the transfer region 14 with the target, a separate hydrating step/process where the microorganisms are hydrated prior to contact with the target or prior to the inoculating/transfer process is not required.

When the target is a liquid (e.g., a liquid broth, a liquid media, a liquid buffer, a saline solution, water, combinations thereof, and the like), the transfer region 14 may be submerged within the liquid. In some instances, the transfer region 14 may be swirled or agitated to facilitate simultaneous hydration and transfer upon contact between the transfer region 14 and the liquid. Again, because the microorganisms are able to become sufficiently hydrated/transferred by simply contacting the transfer region 14 with the liquid, a separate hydrating step/process where the microorganisms are hydrated prior to contact with the target and/or prior to the inoculating/transfer process is not required. In some instances, the device 10 may be tailored for transferring microorganisms to liquid. For example, the device 10 may take the form of a rod having a transfer region (e.g., similar to the transfer region 14) and a handle region (e.g, similar to the handle region 12). In some instances, the rod may comprise a polypropylene rod with silicone tubing at one end that forms the handle region. The transfer region 14 of the device/rod 10 may be contacted with a suitable broth to allow microorganisms to transfer to the broth. The broth may be monitored for presence of turbidity, signifying the successful transfer of microorganisms to the broth. In some instances, the optical density of the broth may be measured, e.g., at a wavelength of 600 nm, to quantify the concentration of microbial cells. In some instances, the device/rod 10 may be used to transfer the microorganisms to a liquid and, optionally, the liquid containing the microorganisms may then be used to inoculate a target (e.g., a growth medium, e.g., a dehydrated growth medium such as PetriFilm™). In some instances, the device/rod 10 may include a cap (e.g., similar to the cap 28 disclosed herein) that can overlie the transfer region 14. The device/rod 10 may also be packaged in a pouch (e.g., similar to the pouch 30 disclosed herein). In some of these and in other instances, the device/rod 10 may not need a cap (e g, similar to the cap 28 disclosed herein).

The disclosure is not intended to limit the device 10 to transferring microorganisms to a solid (e.g., agar) target or liquid media as a number of additional uses are also contemplated. In general, the device 10 may be used for growth promotion testing, environmental control/testing, validation testing (e.g., including validating instruments), as a starter culture, to transfer a known microorganism and/or a known quantity of microorganisms, combinations thereof, and/or the like. In some of these and in other instances, the device 10 may be used as a positive control device. For example, the device 10 may be brought into contact with a sampling device (e.g., a microbial collection device) such as a sample collection sponge or swab such as those used for environmental control/testing. In some instances, the sample collection sponge or swab may be pre-wetted (e.g., pre-wetted by the manufacturer) and the pre-wetted sponge or swab may be contacted with the device 10. After contacting the sampling device with the device 10, the microorganisms may be extracted from the sampling device, e.g., using a solution (e.g., a liquid media). In some instances, after contacting the sponge with the device 10, the sponge may be wrung out/squeezed to remove the pre-wetting solution (e.g., a neutralizing buffer) from the sponge and the pre-wetting solution may be captured/recovered. The captured/recovered solution may be tested for the presence of the microorganisms. The presence of microorganisms in the recovered solution serves as a positive control that signifies/verifies that the microorganisms were successfully transferred to the sponge and that the sponge is suitable for collecting microorganisms (e.g., as part of a test such as environmental control/testing). The quantity of microorganisms in the captured/recovered solution may be evaluated or measured (e.g., by enumeration of colony forming units using a culture media).

In some instances, the device 10 may be understood to be a single use or "disposable" device. In other instances, the device 10 may be understood to a multi-use or reusable device.

Figure 2:
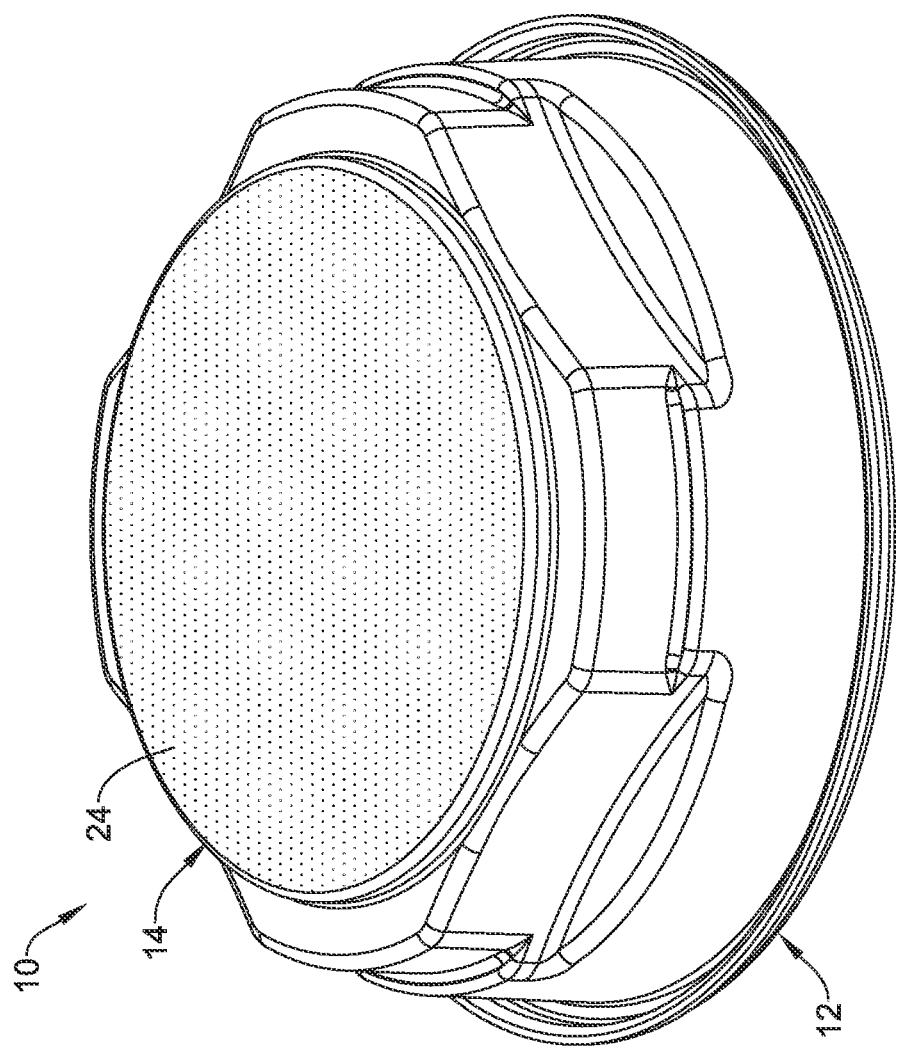
FIG. 2 is a perspective view of an example inoculating device.

As indicated above, the pre-determined quantity of viable microorganisms, schematically depicted in FIG. 2 and denoted with reference number 24, may be disposed on the transfer region 14. In some instances, the pre-determined quantity of viable microorganisms 24 are coated onto the transfer region 14 and then air dried (e.g., the microorganisms are air-dried). In some of these and in other instances, the microorganisms 24 may be freeze-dried, lyophilized, dehydrated, combinations thereof, and/or the like. In some instances, about 1 to 1000 colony forming units of viable microorganisms 24 may be disposed along the transfer region 14, or about 1 to 100 colony forming units of viable microorganisms 24 may be disposed along the transfer region 14.

Figure 3:
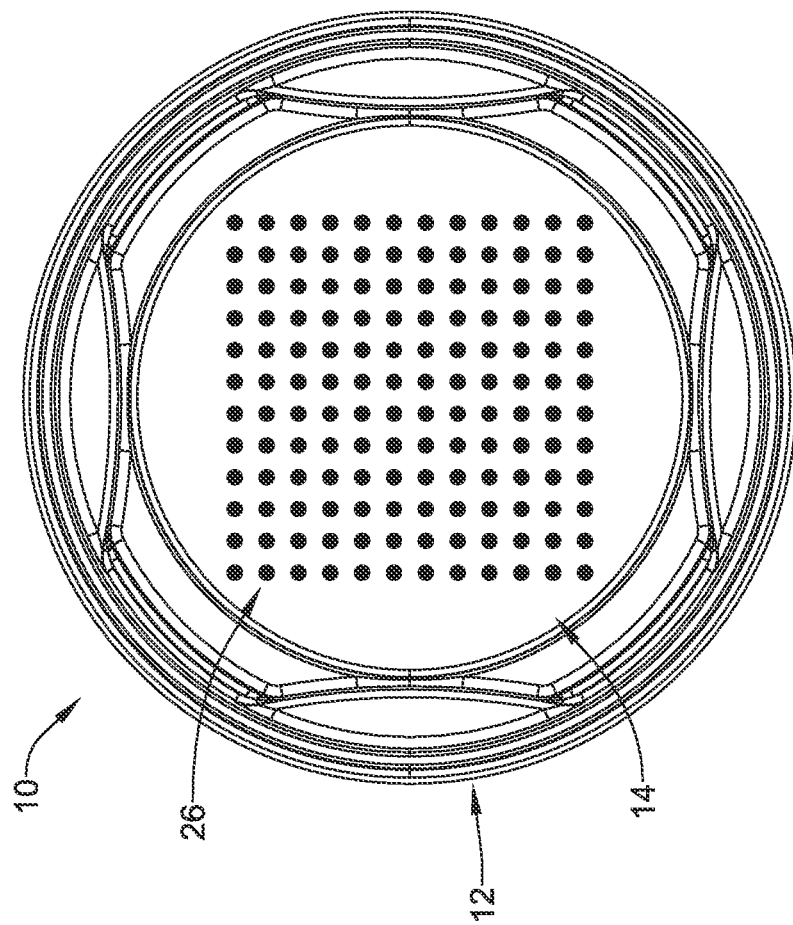
FIG. 3 is a top view of an example inoculating device.

In some instances, the microorganisms 24 may be disposed evenly/homogeneously along the transfer region 14. In some of these and in other instances, the microorganisms 24 may disposed/arranged in a pattern along the transfer region 14. For example, the pattern may include an array of microbial clusters 26 as depicted in FIG. 3. In some instances, the microbial clusters 26 may each include one or more microbial cells that are designed to produce a distinct colony forming unit (e.g., when the transfer region 14 is brought into contact with the target). This may allow for the efficient transfer of discrete colonies/clusters that can be easily visualized by a user following the transfer (e.g., after a suitable incubation period the colonies/clusters can be visualized in the pattern).

Figure 4:
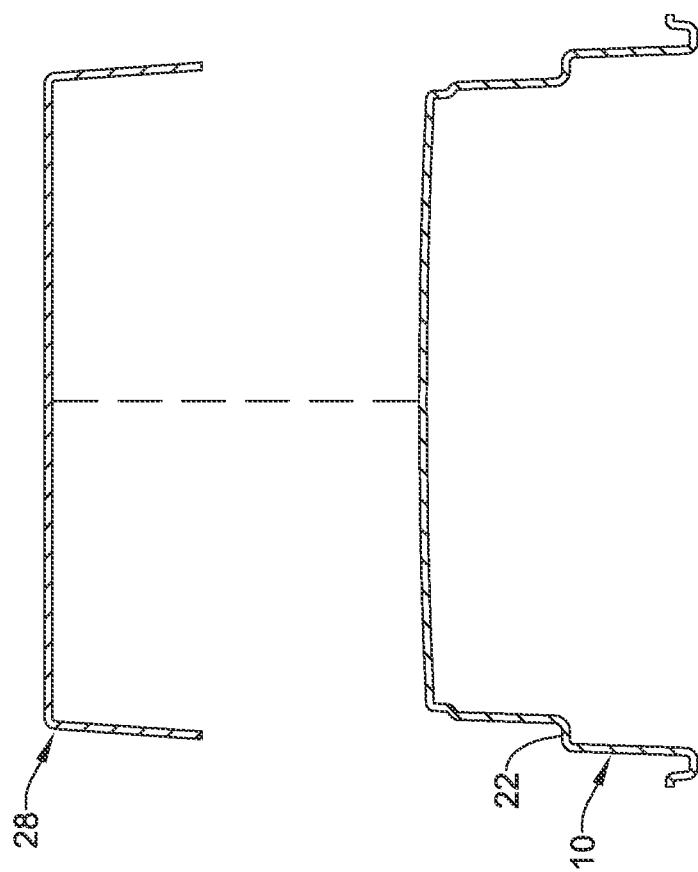
FIGS. 4-5 depict an example inoculating device and an example cap.
Figure 5:
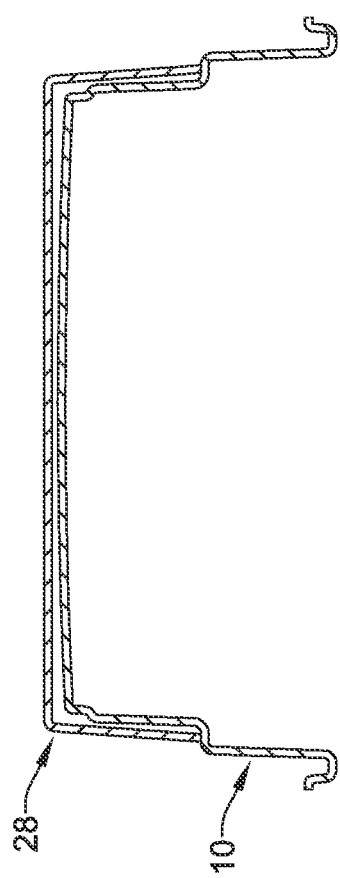
Figure 6:
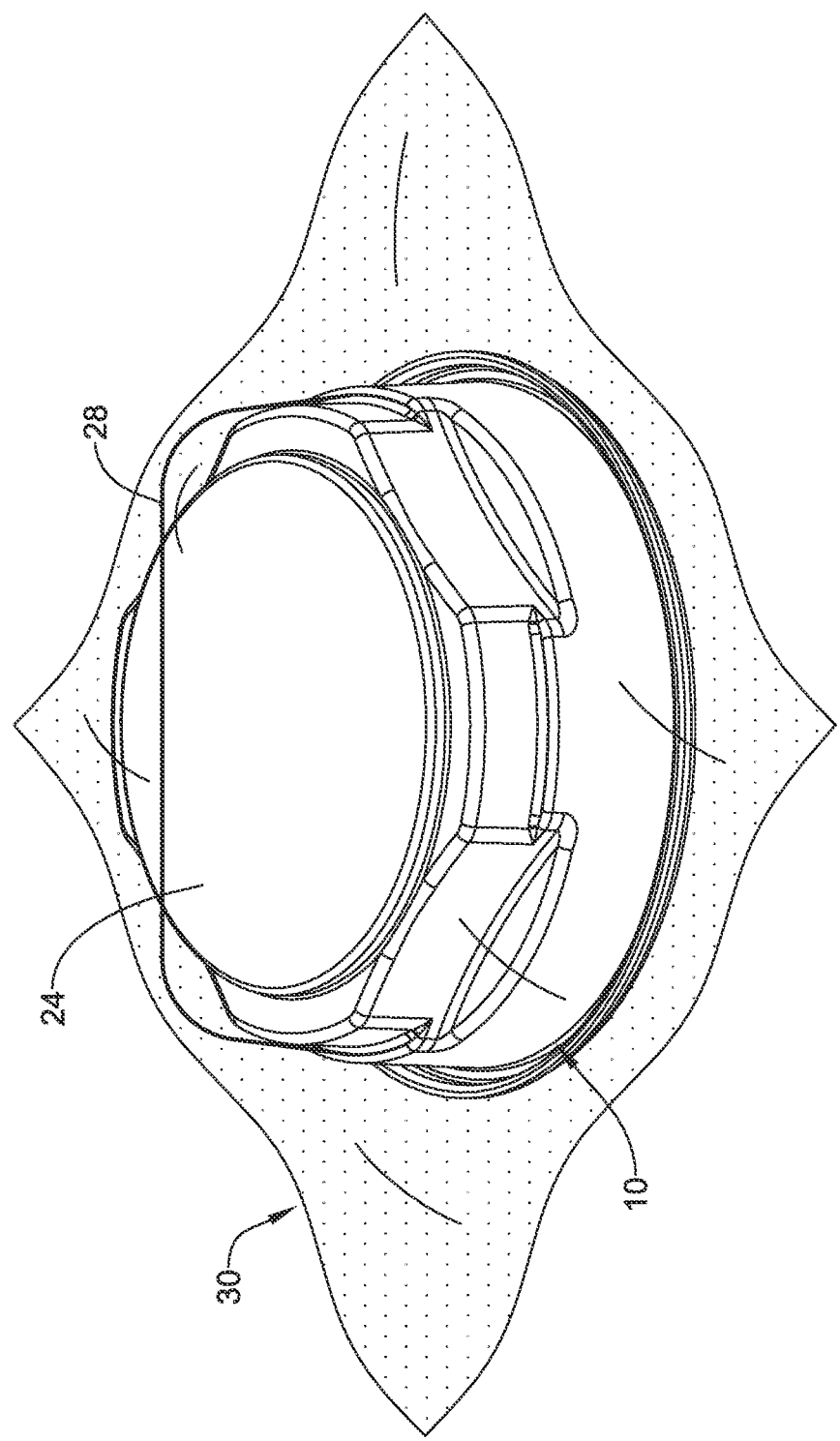
FIG. 6 illustrates an example inoculating device disposed within a package.
Figure 7:
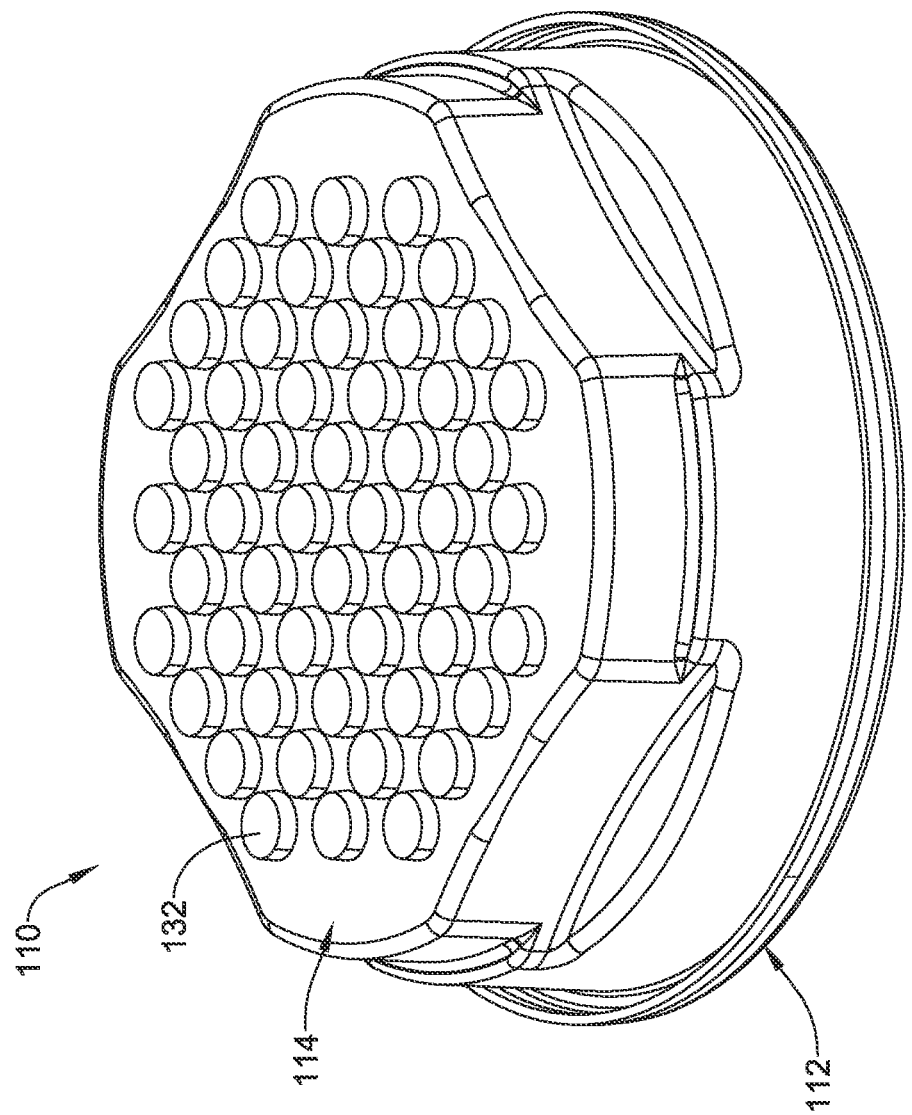
FIG. 7 is a perspective view of an example inoculating device.

In some instances, a cap 28 may be disposed over the transfer region 14 as schematically depicted in FIGS. 4-5. For example, after disposing the microorganisms 24 onto the transfer region 14, the cap 28 may be placed over the transfer region 14. In some instances, this may include placing the edge or lip of the cap 28 along the cap receiving region 16. More particularly, the edge or lip of the cap 28 may be disposed within the grooved region 22. In some instances, the spacer sections 20 may allow for some air flow to occur along the cap receiving region 16. In addition, when the device 10 and cap 28 are disposed within a package/pouch/container (e.g., as described herein), the spacer sections 20 may allow for the atmosphere and/or conditions within the pouch to have access to the microorganisms 24. In some instances, the cap 28 may include a mechanism or system that secures the cap to the device 10. For example, the cap 28 may be threaded and/or have a locking mechanism in conjunction with the device 10.

Once the cap 28 is disposed over the transfer region 14, the device 10 (having the microorganisms 24 along the transfer region 14) may be disposed in a package or pouch 30 as shown in FIG. 6. The package 30 may include airflow and/or moisture resistant materials that are generally designed to control the flow of air and/or moisture into and out from the package 30. For example, the package 30 may include a metal film, metal foil, polymer film (e.g., a stretch or biaxially-oriented polyethylene terephthalate film such as MYLAR), combinations thereof, and/or the like. In some instances, a particular atmosphere such as a modified atmosphere where a gas (e.g., nitrogen) may be used within the package 30. Other atmospheres and/or conditions may be utilized.

In some instances, a desiccant and/or oxygen scavenger may be disposed within the package 30. The quantities of desiccant and/or oxygen scavenger used may help to provide a suitable environment for the microorganisms 24 to have the desired viability. For example, a relatively small amount of desiccant may be added to the package 30. As such, the relative humidity within the package 30 may be 10% or more, or about 20% or more, or about 30% or more, or about 20-30% or more. In addition, a relatively large amount of oxygen scavenger may be added to the package 30. As such, the oxygen level/content within the package may be relatively low. For example, the oxygen content within the package may be about 10% or less, or about 5% or less, or about 4% or less, or about 3% or less, or about 2% or less, or about 1% or less.

The blend of relatively high relative humidity and relatively low oxygen within the package 30 surprising resulted in enhanced viability of the microorganisms 24. For example, a package 30 as described herein has been shown to result in 99% or more viability when stored at an elevated temperature (97° F.) for greater than 90 days. In some instances, the microorganisms 24 are room temperature stable. In some instances, the microorganisms 24 are stable at a temperature of 20° C. or less. In some instances, the microorganisms 24 are stable at a temperature of 4° C. or less. In some instances, the microorganisms 24 have a viability of 50% or more after 30 days. In some instances, the microorganisms 24 have a viability of 50% or more after 90 days. In some instances, the microorganisms 24 have a viability of 50% or more at 20° C. for 90 days. In some instances, the microorganisms 24 have a viability of 75% or more at 20° C. for 90 days. In some instances, the microorganisms 24 have a viability of 90% or more at 20° C. for 90 days.

To use the device 10, the device may be removed from the package 30. This may include cutting open or otherwise unsealing the package. Upon removal, the cap 28 may be removed and the transfer region 14 may be brought into contact with the target. As discussed herein, an additional step of rehydrating the microorganisms 24 prior to the inoculating/transferring step is not required.

FIG. 7 illustrates another example inoculating device 110 that may be similar in form and function to other inoculating devices disclosed herein. The inoculating device 110 may include a handle region 112 and a transfer region 114. A plurality of projections 132 may be disposed along the transfer region 114. The microorganisms (e.g. the microorganisms 24) may be disposed along the projections 132 (e.g., along one or more of the projections 132). In some instances, the microorganisms may only be disposed along the projections 132 (e.g., along the top or end surfaces of the projections 132). In some of these instances, the remainder of the transfer region 114 may be free of the microorganisms. In other instances, the microorganisms may be disposed along both the projections 132 and along other parts of the transfer region 114 (e.g., parts that do not include projections 132).

In some instances, one or more of the projections 132 may have a convex shape and/or otherwise include a surface that is convex. For example, the top or end of the projections 132 may bow outward or otherwise take the form of a convex surface. In some of these and in other instances, one or more of the projections 132 may have a planar shape and/or otherwise includes a surface that is planar. For example, the top or end of the projections 132 may be flat or otherwise take the form of a planar surface. In addition, the remainder of the transfer region 114 may be convex or planar. Thus, in some instances the transfer region 114 may bow outward or otherwise take the form of a convex surface, projections 132 may be disposed along the transfer region 114, and the ends of the projections 132 may also bow outward or otherwise take the form of a convex surface.

The transfer region 114 may include a suitable number of projections 132. For example, the transfer region 114 may include about 2 to 1,000 projections 132, or about 2 to 100 projections 132, or about 2 to 50 projections 132, or about 40 projections. The projections 132 may also have a suitable size. For example, the diameter or a diagonal across the projections 132 may be about 1 mm or more, or about 1 to 25 mm or more, or about 1 to 10 mm or more, or about 1 to 5 mm. The surface area of the projections 132 (e.g., the surface area of the end surface) may be about 0.5 $mm^2$ or more, or about 0.5 to 1,000 $mm^2$, or about 0.5 to 20 $mm^2$. In some instances, the sides or peripheral surfaces of the projections 132 may be rounded, blunt, unsharp, or the like. The projections 132 may have a suitable height. For example, the projections 132 may have a height of 5 mm or less, 4 mm or less, 3 mm or less, 2 mm or less, or 1 mm or less.

The use of a transfer region 114 with projections 132 may be desirable for a number of reasons. For example, the projections 132 may help to reduce the amount of contact between the transfer region 114 and the target. This may help to reduce suction or binding between the transfer region 114 and the target during transfer. For example, if the transfer region 114 was to bind with the target, pulling the transfer region 114 away from the target could bend or deflect the target material. This may result in an uneven or imprecise transfer of microorganisms and/or result in challenges with spreading microorganisms evenly across the target. Thus, the projections 132 may help to reduce/avoid these potential drawbacks during transfer.

Forming the inoculating device 110 (e.g., including the transfer region 114 with projections 132) may include those processes and materials disclosed herein. For example, the inoculating device 110 may be formed using thermoforming, injection molding, molding, casting, and/or the like. In some instances, the inoculating device 110 may be made from materials such as polypropylene, polyethylene, polyethylene terephthalate, glycol modified polyethylene terephthalate, polystyrene, poly-lactic acid, acrylonitrile butadiene styrene, polyetheretherketone, polyoxymethylene, nylon, polycarbonate, polytetrafluoroethylene, or combinations thereof. In one example, the inoculating device 110 may be formed from polypropylene (e.g., via an injection molding process).

Figure 8:
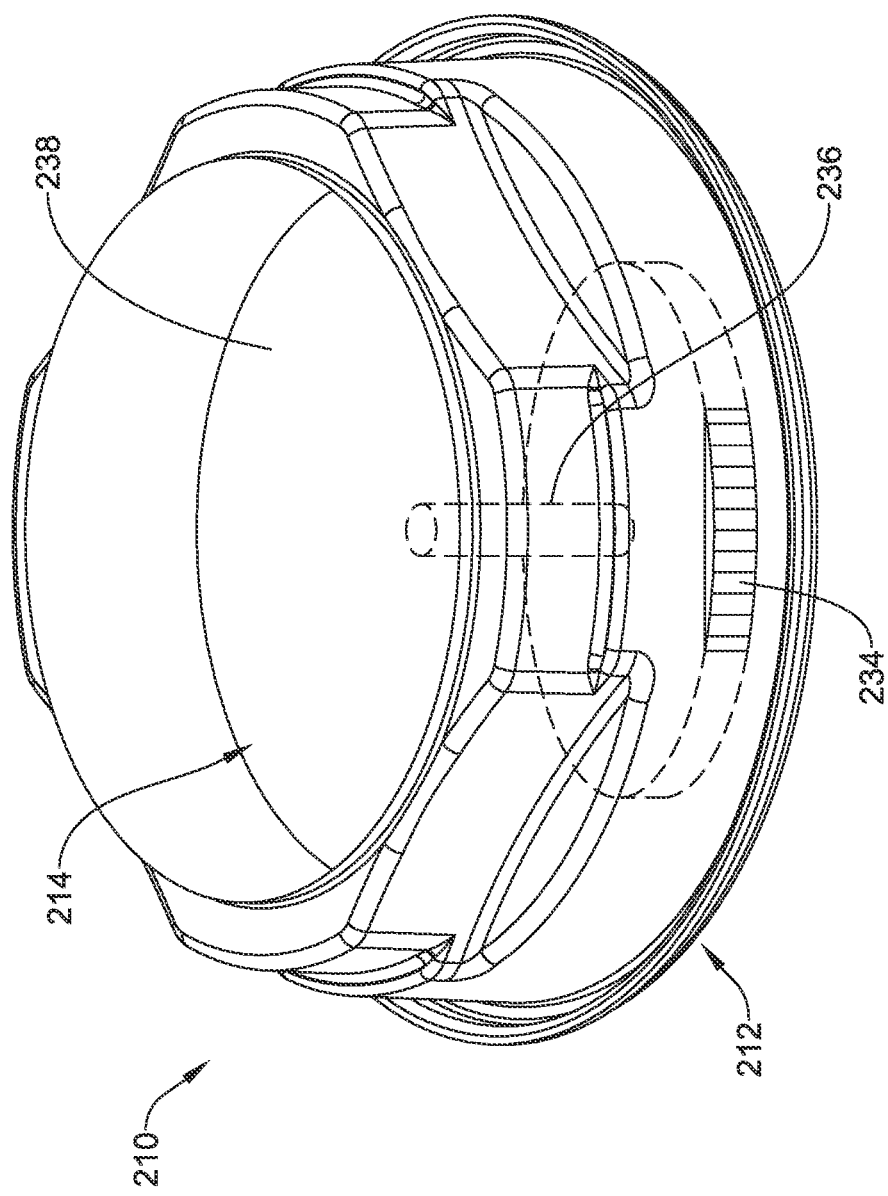
FIG. 8 is a perspective view of an example inoculating device.
Figure 9:
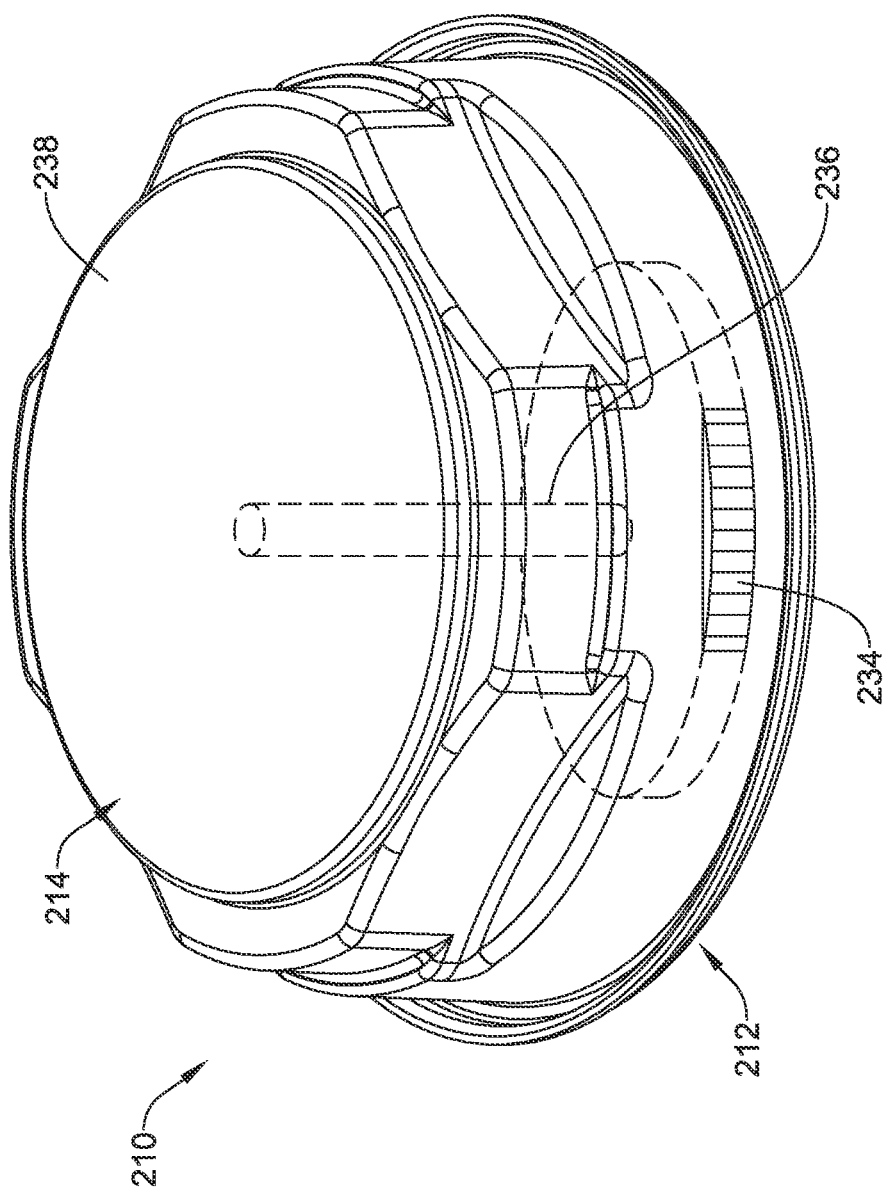
FIG. 9 is a perspective view of an example inoculating device.

FIGS. 8-9 illustrate another example inoculating device 210 that may be similar in form and function to other inoculating devices disclosed herein. The inoculating device 210 may include a handle region 212 and a transfer region 214. In this example, the transfer region 214 may include a moveable platform 238 coupled to an actuator 236 by a rod 236. Actuation of the actuator 236 (e.g., rotation of the actuator 236) may result in the platform 238 raising and lowering. For example, when in a storage configuration such as that shown in FIG. 8, the platform may be recessed or otherwise disposed closer to the handle region 212. When the actuator 236 is actuated, the platform 238 may shift toward a transfer configuration where the platform 238 and/or the transfer region 214 can be utilized to transfer microorganisms to a target.

The process for disposing the microorganisms 24 onto the transfer region 14 may include a number of steps. For example, a cell suspension may be prepared with a known quantity and/or concentration of microorganisms.

The microorganisms in any of the devices, apparatuses, inoculating systems, and methods provided herein can be a prokaryotic organism or a eukaryotic organism. Non-limiting examples of the types of microorganisms that can be included in any of the devices or methods provided herein include: bacteria, fungi, algae, protist, diatom, archaea, and cyanobacteria. In some embodiments, the microorganisms can comprise a single type of microorganism, at least two types of microorganisms, at least three types of microorganisms, at least four types of microorganisms, at least five types of microorganisms, or more than five types of microorganisms.

In some instances, the microorganisms can comprise a homogenous population of identical cells. In some embodiments, the microorganisms can comprise a heterogeneous population of microbial cells. In some embodiments, the microorganisms in any of the devices, apparatuses, inoculating systems, and methods provided herein can comprise one organism, at least two different organisms, at least three different organisms, at least four different organisms, at least five different organisms, at least six different organisms, at least seven different organisms, at least eight different organisms, at least nine different organisms, at least ten different organisms, at least twenty different organisms, at least thirty different organisms, or more than thirty different organisms.

In some embodiments, the microorganisms can comprise one species, at least two species, at least three species, at least four species, at least five species, at least six species, at least seven species, at least eight species, at least nine species, at least ten species, or more than ten species of microorganisms. In some embodiments, the microorganisms can comprise one strain, at least two strains, at least three strains, at least four strains, at least five strains, at least six strains, at least seven strains, at least eight strains, at least nine strains, at least ten strains, at least fifteen strains, at least twenty strains, at least twenty-five strains, at least thirty strains, at least thirty-five strains, at least forty strains, at least forty-five strains, at least fifty strains, or more than fifty strains of microorganisms. In some examples, the microorganisms include a gram-positive bacteria or a gram-negative bacteria. In some examples, the microorganisms include a fungi (e.g., a yeast). The microorganisms in any of the devices, apparatuses, inoculating systems, and methods provided herein can include a spore.

In some embodiments, the microorganism is selected from the group of: *Acetobacter* spp., *Acetonema* spp., *Achromobacter* spp., *Acidithiobacillus* spp., *Acinetobacter* spp., *Actinobacillus* spp., *Actinomyces* spp., *Aerococcus* spp., *Aeromonas* spp., *Aggregatibacter* spp., *Agrobacterium* spp., *Alcaligenes* spp., *Alicyclobacillus* spp., *Alkalibacillus* spp., *Alternaria* spp., *Ammoniphilus* spp., *Amphibacillus* spp. *Anaerobacter* spp., *Anaerospora* spp., *Anaplasma* spp., *Aneurinibacillus* spp., *Anoxybacillus* spp., *A rcanobacierium* spp., *Arthrobacter* spp., *Aspergillus* spp., *Aureobasidium* spp. *Azorhizobium* spp., *Azotobacter* spp., *Bacillus* spp., *Bacteroides* spp., *Bartonella* spp. *Beggiatoa* spp., *Bifidobacterium* spp., *Brevibacierium* spp., *Brevibacillus* spp., *Brevundimonas* spp., *Bordetella* spp., *Borrelia* spp., *Brochothrix* spp., *Brucella* spp., *Burkholderia* spp., *Caldanaerobacter* spp., *Caloramator* spp., *Calymmatobacterium* spp., *Caminicella* spp., *Campylobacter* spp., *Candida* spp., *Capnocytophaga* spp., *Cedecea* spp., *Cellulosimicrobium* spp., *Cerasibacillus* spp., *Chaetomium* spp., *Chlamydia* spp., *Chlamydophila* spp., *Chryseobacterium* spp., *Citrobacter* spp., *Cladosporium* spp., *Clostridioides* spp., *Clostridium* spp., *Clostridiisalibacter* spp., *Cohnella* spp., *Corynebacterium* spp., *Coxiella* spp., *Cronobacter* spp., *Cryptococcus* spp., *Curtobacterium* spp., *Cutibacterium* spp., *Deinococcus* spp., *Dendrosporobacter* spp., *Desubrotomacuium* spp., *Desulfosporomusa* spp., *Desulfosporosinus* spp., *Desulfovibrio* spp., *Desulfovirgula* spp., *Desulfunispora* spp., *Desulfurispora* spp., *Edwardsiella* spp., *Eggerthella* spp., *Ehrlichia* spp., *Eikenella* spp., *Elizabethkingia* spp., *Enterobacter* spp., *Enterococcus* spp., *Erysipelothrix* spp., *Escherichia* spp., *Eurotium* spp., *Ferrobacillus* spp., *Filifactor* spp., *Filobacillus* spp., *Finegoldia* spp., *Fluoribacter* spp., *Francisella* spp., *Fusarium* spp., *Fusobacterium* spp., *Gallionella* spp., *Gardnerella* spp., *Gelria* spp., *Geobacillus* spp., *Geosporobacter* spp., *Geotrichum* spp., *Gracilibacillus* spp., *Haemophilus* spp., *Hafnia* spp., *Halobacillus* spp., *Halonatronum* spp., *Hanseniaspora* spp., *Helicobacter* spp., *Heliobacterium* spp., *Heliophilum* spp., *Herminiimonas* spp. *Hormoconis* spp., *Issatchenkia* spp., *Klebsiella* spp., *Kocuria* spp., *Laceyella* spp., *Lactobacillus* spp., *Lactococcus* spp., *Legionella* spp., *Lentibacillus* spp., *Leptothrix* spp., *Listeria* spp., *Lysinibacillus* spp., *Malassezia* spp., *Mannheimia* spp., *Mahella* spp., *Megasphaera* spp., *Metabacterium* spp., *Methanobacterium* spp., *Methylobacterium* spp., *Meyerozyma* spp., *Microbacterium* spp., *Micrococcus* spp., *Microsporum* spp., *Moorella* spp., *Moraxella* spp., *Morganella* spp., *Mucor* spp., *Mycobacterium* spp., *Mycoplasma* spp., *Myroides* spp., *Natroniella* spp., *Neisseria* spp., *Nocardia* spp., *Oceanobacillus* spp., *Ochrobactrum* spp., *Oligella* spp., *Orenia* spp., *Ornithinibacillus* spp., *Oxalophagus* spp., *Oxobacter* spp., *Paenibacillus* spp., *Parabacteroides* spp., *Paraliobacillus* spp., *Parvimonas* spp., *Pasteurella* spp., *Pediococcus* spp., *Pelospora* spp., *Pelotomaculum* spp., *Penicillium* spp., *Peptostreptococcus* spp., *Piscibacillus* spp., *Planifilum* spp., *Pluralibacter* spp., *Pneumocystis* spp., *Pontibacillus* spp., *Porphyromonas* spp., *Prevotella* spp., *Propionibacterium* spp., *Propionispora* spp., *Proteus* spp., *Prototheca* spp., *Providencia spp., *Pseudomonas* spp., *Ralstonia* spp., *Raoultella* spp., *Rhizobium* spp., *Rhizopus* spp., *Rhodococcus* spp., *Rickettsia* spp., *Rochalimaea* spp., *Rothia* spp., *Saccharomyces* spp., *Salinibacillus* spp., *Salmonella* spp., *Salsuginibacillus* spp., *Seinonella* spp., *Serratia* spp., *Shewanella* spp., *Shigella* spp., *Shimazuella* spp., *Sinorhizobium* spp., *Sphingobacterium* spp., *Sphingomonas* spp., *Spirillum* spp., *Sporacetigenium* spp., *Sporidiobolus* spp., *Sporoanaerobacter* spp., *Sporobacter* spp., *Sporobacterium* spp., *Sporohalobacter* spp., *Sporolactobacillus* spp., *Sporomusa* spp., *Sporosarcina* spp., *Sporotalea* spp., *Sporotomaculum* spp., *Staphylococcus* spp., *Stenotrophomonas* spp., *Stomatococcus* spp., *Streptococcus* spp., *Streptomyces* spp., *Syntrophomonas* spp., *Syntrophospora* spp., *Talaromyces* spp., *Tenuibacillus* spp., *Tepidibacter* spp., *Terribacillus* spp., *Thalassobacillus* spp., *Thermoacetogenium* spp., *Thermoactinomyces* spp., *The rmoalkalibacillus* spp., *Thermoanaerobacter* spp., *Thermoanaerobacterium* spp., *Thermoanaeromonas* spp., *Thermobacillus* spp., *Thermoflavimicrobium* spp., *Thermovenabulum* spp., *Thiobacillus* spp., *Thiothrix* spp., *Treponema* spp., *Trichophyton* spp., *Trichosporon* spp., *Trueperella* spp., *Tuberibacillus* spp., *Ureaplasma* spp., *Veillonella* spp., *Vibrio* spp., *Virgibacillus* spp., *Viridans* spp., *Vulcanobacillus* spp., *Wallemia* spp., *Wolbachia* spp., *Yarrowia* spp., *Yersinia* spp., and *Zygosaccharomyces* spp.

In some embodiments, the microorganism is selected from the group of: *Acetobacter aurantius, Acidithiobacillus thiooxidans, Acinetobacter baumannii* (e.g., ATCC® 19606™), *Actinomyces israelii, Agrobacterium radiobacter, Agrobacterium tumefaciens, Anaplasma phagocytophilum, Arthrobacter chlorophenolicus, Arthrobacter crystallopoietes, Arthrobacter luteus, Aspergillus brasiliensis* (e.g., ATCC® 16404™), *Aspergillus flavus* (e.g., ATCC® 9643™), *Aspergillus fumigatus* (e.g., ATCC® 204305™), *Aspergillus niger* (e.g., ATCC® 6275™), *Aspergillus terreus* (e.g., ATCC® 1012™), *Aureobasidium pullulans, Azorhizobium caulinodans, Azotobacter vinelandii, Bacillus anthracis, Bacillus atrophaeus, Bacillus brevis, Bacillus cereus, Bacillus fusiformis, Bacillus licheniformis, Bacillus megaterium, Bacillus mycoides, Bacillus stearothermophilus, Bacillus subtilis* (e.g., ATCC® 6633™), *Bacillus thuringiensis, Bacteroides fragilis, Bacteroides gingivalis, Bartonella henselae, Bartonella quintana, Beggiatoa alba, Bordetella bronchiseptica, Bordetella pertussis* (e.g., ATCC® 12743™), *Borrelia burgdorferi, Brevundimonas diminuta* (e.g., ATCC® 19146™), *Brucella abortus, Brucella melitensis, Brucella suis, Burkholderia mallei, Burkholderia pseudomallei, Burkholderia cepacia* (e.g., ATCC® 25416™), *Calymmatobacterium granulomatis, Campylobacter coli, Campylobacter fetus, Campylobacter jejuni* (e.g., ATCC® 33291™ and ATCC® 29428™), *Campylobacter pylori, Candida albicans* (e.g., ATCC® 2091™ and ATCC® 10231™), *Candida auris, Candida dubliniensis, Candida krusei, Candida glabrata, Candida lusitaniae, Candida parapsilosis, Candida tropicalis, Chlamydia trachomatis, Chlamydophila pneumoniae, Chlamydophila psittaci, Cladosporium cladosporioides, Cladosporium resinae, Clostridium botulinum, Clostridium difficile* (e.g., ATCC® 43598™), *Clostridium perfringens, Clostridium sporogenes* (e.g., ATCC® 11437™ and ATCC® 19404™), *Clostridium tetani, Corynebacterium ammoniagenes, Corynebacterium diphtheriae, Corynebacterium fusiforme, Corynebacterium glutamicum, Corynebacterium stationis, Coxiella burnetii, Cronobacter sakazakii* (e.g., ATCC® 12868™), *Cryptococcus neoformans, Desulfovibrio africanus, Desulfovibrio desulfuricans, Desulfovibrio salixigens, Desulfovibrio vulgaris, Desulfotomaculum orientis, Desulfotomaculum nigrificans, Ehrlichia chaffeensis, Enterobacter aerogenes* (e.g., ATCC® 13048™), *Enterobacter cloacae, Enterococcus avium, Enterococcus durans, Enterococcus faecalis* (e.g., ATCC® 29212™ and ATCC® 51575™), *Enterococcus faecium* (e.g., ATCC® 35667™ and ATCC® 51559™), *Enterococcus gallinarum, Enterococcus hirae, Enterococcus maloratus, Escherichia coli* (e.g., ATCC® 8739™, ATCC® 25922™, ATCC® 10536™, ATCC® 11229™, and ATCC® 35150™), *Ferrobacillus ferrooxidans, Fluoribacter bozemanae, Francisella tularensis, Fusobacterium nucleatum, Gallionella ferruginea, Gardnerella vaginalis, Geobacillus stearothermophilus, Haemophilus ducreyi, Haemophilus influenzae* (e.g., ATCC® 10211™), *Haemophilus parainfluenzae, Haemophilus pertussis, Haemophilus vaginalis, Helicobacter pylori, Hormoconis resinae, Klebsiella oxytoca* (e.g., ATCC® 13182™), *Klebsiella pneumoniae* (e.g., ATCC® 4352™ and ATCC® 51503™), *Kocuria rhizophila* (e.g., ATCC® 9341™), *Lactobacillus acidophilus, Lactobacillus bulgaricus, Lactobacillus casei, Lactobacillus plantarum, Lactococcus lactis, Legionella pneumophila* (e.g., ATCC® 33153™), *Leptothrix ochracea, Leptothrix discophora, Leptothrix cholodnii, Leptothrix lopholea, Leptothrix mobilis, Listeria monocytogenes* (e.g., ATCC® 19117™, ATCC® 19111™, and ATCC® 7644™), *Methanobacterium extroquens, Microbacterium multiforme, Micrococcus luteus, Moraxella catarrhalis, Moraxella osloensis, Mycobacterium avium, Mycobacterium bovis* (e.g., ATCC® 35743™), *Mycobacterium diphtheriae, Mycobacterium intracellulare, Mycobacterium leprae, Mycobacterium lepraemurium, Mycobacterium phlei, Mycobacterium smegmatis, Mycobacterium terrae* (e.g., ATCC® 15755™), *Mycobacterium tuberculosis, Mycoplasma fermentans, Mycoplasma genitalium, Mycoplasma hominis, Mycoplasma penetrans, Mycoplasma pneumoniae, Mycoplasma mexican, Neisseria gonorrhoeae, Neisseria meningitidis, Paenibacillus glucanolyticus, Pasteurella multocida, Pasteurella tularensis, Penicillium chrysogenum, Pluralibacter gergoviae, Pneumocystis carinii, Pneumocystis murina, Porphyromonas gingivalis, Prevotella melaninogenica, Proteus mirabilis* (e.g., ATCC® 9240™), *Proteus vulgaris, Pseudomonas aeruginosa* (e.g., ATCC® 9027™ and ATCC® 15442™), *Pseudomonas fluorescens, Pseudomonas putida, Ralstonia pickettii, Rhizobium leguminosarum, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella bongori, Salmonella carrau, Salmonella concord, Salmonella enterica* (e.g., ATCC® 10708™, ATCC® 6539™, ATCC® 4931™, ATCC® 13311™, and ATCC® 14028™), *Salmonella enteritidis, Salmonella infantis, Salmonella newport, Salmonella schwarzengrund, Salmonella typhi, Salmonella typhimurium, Serratia marcescens* (e.g., ATCC® 14756™ and ATCC® 8100™), *Shewanella oneidensis, Shewanella putrefaciens, Shigella dysenteriae* (e.g., ATCC® 11835™), *Shigella flexneri* (e.g., ATCC® 29508™), *Shigella sonnei* (e.g., ATCC® 11060™ and ATCC® 25931™), *Sinorhizobium meliloti, Spirillum volutans, Staphylococcus aureus* (e.g., ATCC® 6538™, ATCC® 29737™, ATCC® BAA-1683™, and ATCC® 33592™), *Staphylococcus epidermidis* (e.g., ATCC® 12228™), *Staphylococcus hominis, Staphylococcus saprophyticus, Stenotrophomonas maltophilia, Stomatococcus mucilaginous, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus gor-*

*donii, Streptococcus lactis, Streptococcus mitior, Streptococcus mitis, Streptococcus mutans, Streptococcus oralis, Streptococcus pneumoniae* (e.g., ATCC® 6305™), *Streptococcus pyogenes* (e.g., ATCC® 12384™ and ATCC® 19615™), *Streptococcus rattus, Streptococcus salivarius, Streptococcus sanguis, Streptococcus sobrinus, Thiobacillus concretivorus, Thiobacillus thioparus, Treponema pallidum, Treponema denticola, Trichophyton interdigitale* (e.g., ATCC® 9533™), *Trichophyton mentagrophytes* (e.g., ATCC® 9533™), *Trichosporon asahii, Vibrio cholerae* (e.g., ATCC® 11623™), *Vibrio comma, Vibrio parahaemolyticus, Vibrio vulnificus, Viridans streptococci, Yersinia enterocolitica* (e.g., ATCC® 23715™), *Yersinia pestis*, and *Yersinia pseudotuberculosis*, including drug-resistant strains thereof. Additional microorganisms that can be included in any of the devices or methods provided herein are contemplated.

The microorganisms may be naturally occurring or genetically modified. In some instances, the microorganism may be genetically modified, e.g., to exhibit fluorescence under certain conditions. The microorganism may be sourced from a laboratory collection or an environmental sample. In some examples, the microorganism is sourced from a preserved collection of reference microorganisms (e.g., ATCC®, NCTC, NCIMB, WDCM, CECT, NCPF, DSM, NBRC, ACM, or IMVS). In other instances, the microorganism is isolated from an environmental sample, e.g., from a human subject or from a surface in a manufacturing facility. Other sources and other methods of collecting and isolating microorganisms are known in the art and may be utilized.

A stabilizing mixture comprising stabilizing agents can be added to the known quantity/concentration of microorganisms. The stabilizing agents can be included to improve the stability of the microorganisms through the coating/drying process and over time in storage. In some embodiments, an additive may be included to improve other properties of the device and its use, e.g., the transfer efficiency of the microorganisms from the device to a target. Any of the exemplary stabilizing agents provided herein may be included as an additive to modify properties other than stability. Additional additives that can be included to modify properties other than stability are also contemplated.

Non-limiting examples of stabilizing agents that can be included in any of the devices and methods provided herein include: a sugar (e.g., a monosaccharide, a disaccharide, a reducing sugar, or a non-reducing sugar), a polyol, a polymer (e.g., an oligosaccharide, a polysaccharide, a cellulose-derivative, or a synthetic polymer), an antioxidant, an amino acid, a surfactant, and a buffer.

Non-limiting examples of sugars that can be included in any of the devices and methods provided herein include: glucose, fructose, xylose, arabinose, sorbose, mannose, rhamnose, galactose, trehalose, maltose, lactose, sucrose, melibiose, maltulose, iso-maltulose, and lactulose.

Non-limiting examples of polymers that can be included in any of the devices and methods provided herein include: raffinose, stachyose, melezitose, mannotriose, maltodextrin, dextran, starch, inulin, ficoll, alginate, chitosan, methylcellulose, hydroxypropyl cellulose, hydroxyethyl cellulose, hypromellose, xanthan gum, guar gum, pectin, carrageen, galactomannan, gellan gum, cellulose acetate phthalate, carboxy-methyl-cellulose, a salt of alginic acid (e.g., sodium alginate), hydroxyl propyl methyl cellulose, gum acacia, locust bean gum, hydroxyethyl cellulose, hydroxypropyl methylcellulose, polyvinyl alcohol, polyvinyl pyrrolidone, gelatin (e.g., hydrolyzed gelatin and unhydrolyzed gelatin), and polyglycolic acid.

Non-limiting examples of polyols that can be included in any of the devices and methods provided herein include: sorbitol, arabitol, xylitol, mannitol, erythritol, threitol, and glycerol.

Non-limiting examples of antioxidants that can be included in any of the devices and methods provided herein include: ascorbic acid, citric acid, acetic acid, a tocopherol, propyl gallate, tertiary butylhydroquinone, butylated hydroxyanisole, and butylated hydroxytoluene.

Non-limiting examples of amino acids that can be included in any of the devices and methods provided herein include: glycine betaine, sodium glutamate, cysteine, cystine, histidine, and methionine.

Non-limiting examples of buffers that can be included in any of the devices and methods provided herein include: a potassium phosphate (e.g., monopotassium phosphate), a sodium phosphate (e.g., monosodium phosphate and disodium phosphate), sodium acetate, sodium citrate, sodium succinate, histidine, imidazole, ammonium bicarbonate, a carbonate, [Tris(hydroxymethyl)methylamino]propanesulfonic acid (TAPS), 2-(Bis(2-hydroxyethyl)amino)acetic acid (Bicine), Tris(hydroxymethyl)aminomethane (Tris), 3-[N-Tris(hydroxymethyl)methylamino]-2-hydroxypropanesulfonic acid (Tricine), 3-[N-Tris(hydroxymethyl)methylamino]-2-hydroxypropanesulfonic acid (TAPSO), 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), 3-(N-morpholino)propanesulfonic acid (MOPS), Piperazine-N,N'-bis(2-ethanesulfonic acid) (PIPES), Dimethylarsenic acid (Cacodylate), 2-(N-morpholino)ethanesulfonic acid (MES), and N-cyclohexyl-2-aminoethanesulfonic acid (CHES).

Non-limiting examples of surfactants that can be included in any of the devices and methods provided herein include: a polysorbate (e.g., polysorbate 20, polysorbate 40, polysorbate 60, or polysorbate 80), a poloxamer (e.g., PLURONICS™), Triton X-100, polyethylene glycol, polypropylene glycol, polyethylene glycol/polypropylene glycol block copolymers, polyethylene glycol alkyl ethers, polypropylene glycol alkyl ethers, and polyethylene glycol/polypropylene glycol ether block copolymers.

Non-limiting examples of other stabilizing agents that can be included in any of the devices and methods provided herein include: milk (e.g., skimmed milk), monosodium glutamate, liquid growth medium, and propylene glycol. Other stabilizing agents that can be included in any of the devices or methods provided herein are contemplated.

In some instances, the stabilizing mixture may include a sugar. For example, the stabilizing mixture may include a non-reducing sugar such as sucrose. In some instances, the stabilizing mixture may include about 0.1% to about 15% of a stabilizing agent, for example, a sugar or a polyol (e.g., about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1%). In some of these and in other instances, the stabilizing mixture may include an antioxidant. In some instances, the stabilizing mixture may include about 0.01% to about 10% of an antioxidant (e.g., about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1%, or about 0.1% to about 0.5%). In some of these and in other instances, the stabilizing mixture may include ascorbic acid. In some of these and in other instances, the stabilizing mixture may include a surfactant. In some instances, the stabilizing mixture may include about 0.001% to about 2% of a surfactant (e.g., about 0.001% to about 1.9%, about 0.001% to about 1.8%, about 0.001% to about 1.7%, about 0.001% to about 1.6%, about 0.001% to about 1.5%, about 0.001% to about 1.4%, about 0.001% to about 1.3%, about 0.001% to about 1.2%, about 0.001% to about 1.1%, about 0.001% to about 1.0%, about 0.001% to about 0.9%, about 0.001% to about 0.8%, or about 0.001% to about 0.7%, about 0.001% to about 0.6%, about 0.001% to about 0.5%, about 0.001% to about 0.4%, about 0.001% to about 0.3%, about 0.001% to about 0.2%, about 0.001% to about 0.1%, or about 0.001% to about 0.01%). For example, the stabilizing mixture may include a nonionic surfactant such as Triton X-100. In some of these and in other instances, the stabilizing mixture may include an amino acid. In some of these and in other instances, the stabilizing mixture may include a protein. In some of these and in other instances, the stabilizing mixture may include a salt. In some of these and in other instances, the stabilizing mixture may include a polymer. In some of these and in other instances, the stabilizing mixture may include a buffer. For example, the stabilizing mixture may include a phosphate buffer such as phosphate buffered saline. In some of these and in other instances, the stabilizing mixture may include tris(hydroxymethyl)aminomethane. In some of these and in other instances, the stabilizing mixture may include 2-[4-(2,4,4-trimethylpentan-2-yl)phenoxy]ethanol. In some of these and in other instances, the stabilizing mixture may include a growth nutrient. In some of these and in other instances, the stabilizing mixture may include a broth. In one embodiment, the stabilizing mixture includes 8-12% of a sugar (e.g., a non-reducing sugar, e.g., sucrose), 5-7% of an antioxidant (e.g., ascorbic acid), and 0.01-0.1% of a surfactant (e.g., Triton X-100). In a preferred embodiment, the stabilizing mixture includes 10% of a sugar (e.g., a non-reducing sugar, e.g., sucrose), 6% of an antioxidant (e.g., ascorbic acid), and 0.04% of a surfactant (e.g., Triton X-100). In another embodiment, the stabilizing mixture includes between 12-15% of a sugar (e.g., a non-reducing sugar, e.g., sucrose), 5-10% of an antioxidant (e.g., ascorbic acid), and optionally 0.01-0.1% of a surfactant (e.g., Triton X-100).

A suitable volume of the stabilizing mixture mixed with the known quantity/concentration of microorganisms (e.g., which may be referred to as the coating solution or mixture) may be disposed on the transfer region 14. For example, 1-10 microliters of the coating solution may be disposed onto the transfer region 14. This may include pipetting the coating solution onto the transfer region 14.

In some embodiments of any of the devices, apparatuses, and inoculating systems provided herein, a volume of between 1 to 200 microliters of the coating solution may be applied onto the transfer region 14. In some embodiments, 5 microliters or less (e.g., 4 microliters or less, 3 microliters or less, 2 microliters or less, 1 microliters or less, 900 nanoliters or less, 800 nanoliters or less, 700 nanoliters or less, 600 nanoliters or less, 500 nanoliters or less, 400 nanoliters or less, 300 nanoliters or less, 200 nanoliters or less, 100 nanoliters or less, 50 nanoliters or less, 25 nanoliters or less, 10 nanoliters or less, 1 nanoliter or less, 900 picoliters or less, 800 picoliters or less, 700 picoliters or less, 600 picoliters or less, 500 picoliters or less, 400 picoliters or less, 300 picoliters or less, 200 picoliters or less, 100 picoliters or less, 50 picoliters or less, 25 picoliters or less, or 10 picoliters or less) of the coating solution is applied onto the transfer region. In some instances, the volume of coating solution may be applied to the transfer region in a single application or by multiple applications.

In some instances, a spreading device may be used to spread the coating solution along the transfer region 14. However, spreading is not required. The coating solution may be allowed to air dry (e.g., dry at room temperature) for a suitable time period such as 1-60 minutes. In some embodiments of any of the devices, apparatuses, and inoculating systems provided herein, the coating solution may be allowed to air dry for 1-50 minutes, 1-45 minutes, 1-40 minutes, 1-35 minutes, 1-30 minutes, 1-25 minutes, 1-20 minutes, 1-15 minutes, 1-10 minutes, 1-5 minutes, or 1 minute or less. In some embodiments of any of the devices, apparatuses, and inoculating systems provided herein, the coating solution may be allowed to air dry at room temperature. In other embodiments, the coating solution may be allowed to air dry at an elevated temperature (e.g., between 25° C. to 40° C.).

In some embodiments of any of the devices, apparatuses, and inoculating systems provided herein, the quantity of microorganisms coated onto the transfer region can be 1-100 CFU, 1-1,000 CFU, or greater than 1,000 CFU. In other embodiments of any of the devices apparatuses, and inoculating systems provided herein, the quantity of viable microorganisms coated onto the transfer region is not known and/or is not pre-determined. In other embodiments, the quantity of viable microorganisms coated onto the transfer region comprises at least one viable microorganism. In some embodiments of any of the devices, apparatuses, and inoculating systems provided herein, no microorganisms are coated onto the transfer region of the device or onto any other part of the device, and the device is used to spread microorganisms that have otherwise been deposited onto a target.

In some examples after drying the inoculating system can comprise between about 0% to about 10% (e.g., between 0% to 5%, between 0% to 2.5%, or between 0% to 1%) of residual water content or residual moisture content by weight (e.g., w/w). In some examples, the pre-determined quantity of microorganisms has a viability of 25% or more after 30 days (e.g., 30% of more after 30 days, 40% of more after 30 days, 50% of more after 30 days, 60% of more after 30 days, 70% of more after 30 days, 80% of more after 30 days, 90% of more after 30 days, or 100% of more after 30 days).

In some embodiments of any of the devices, apparatuses, and inoculating systems provided herein, the transfer region and/or the projection(s) along the transfer region is convex and is curved or rounded outward like the exterior of a sphere or circle.

The transfer of microorganisms to a target from any of the devices, apparatuses, and/or inoculating systems provided herein can be described in part by microbial transfer efficiency or efficacy. It can be appreciated that some microorganisms may be lost while coating onto the transfer region and/or during drying. For the purposes of this disclosure, the transfer efficiency or efficacy may be understood to be the percentage of viable microorganisms disposed on the transfer region that are transferred to the target during an inoculation. In other words, the transfer efficiency or efficacy is the percentage of dried viable microorganisms that are successfully transferred from the transfer region to the target during an inoculation. In some embodiments, the microbial transfer efficiency may be about 50% or more, or about 55% or more, or about 60% or more, or about 65% or more, or about 70% or more, or about 75% or more, or about 80% or more, or about 85% or more, or about 90% or more, or about 95% or more, or about 99% or more, or about or nearly 100%.

EXAMPLES

The disclosure may be further clarified by reference to the following Examples, some of which are prophetic in nature, and serve to exemplify some embodiments, and not to limit the disclosure in any way.

Example 1—Device for Direct-Transfer of Bacterial Cells to Agar Media

*Staphylococcus aureus* (ATCC® 6538™) was grown in nutrient broth for 48 hours at 35° C. The culture was then diluted 5.0E-4 into the coating solution. The coating solution contained synthetic broth (HiMedia M334-500G), sucrose (1% w/v, Aldon Corporation IS28231), and Triton X-100 (0.04% v/v, Electron Microscopy Sciences 22140) in DI water. The coating solution was prepared by first adding synthetic broth powder to DI water (16.9 g/L) followed by steam sterilization of the media. Sucrose was then added to the synthetic broth and dissolved to yield 1% w/v. Then Triton X-100 was added to the solution to yield 0.04% Triton X-100. This solution was then filter sterilized and the *S. aureus* cells were diluted into it in order to target <100 CFU/10 µL volume.

The devices were prepared by cutting circles (1.2" diameter) of polyester film (PET) with adhesive backing (McMaster-Carr 8689K44), pealing the release liner from the back of the PET film and adhering the film to a polypropylene 50 mL conical tube cap (1.25" diameter, 0.5" tall). The assembled devices were then steam sterilized at 121° C. for 20 minutes.

The prepared coating solution was then dispensed (10 µL) onto the surface of the sterilized device and spread over the surface of the PET film with a sterile microbiology spreading rod. The coated devices were then dried at 36° C. for approximately 20 minutes or until the water in the coating solution was substantially evaporated. The devices may then be placed into a moisture barrier package such as an aluminum mylar pouch that also contains a desiccant and oxygen scavenger.

The assembled devices may then be removed from the packaging material. The devices (n=3) were then directly contacted to the surface of trypticase soy agar (TSA) media in a petri dish so that the coated surface of the device was in contact with the surface of the agar media. The device was contacted to the TSA surface for approximately 5 seconds to allow the *S. aureus* cells to transfer from the surface of the device to the surface of the agar. The devices were then disposed and the inoculated TSA petri dish was placed into a 35° C. incubator for approximately 18 hours. The colony counts are shown in Table 1.

TABLE 1

Colony Forming Units (CFUs) after direct transfer from device.

| Device # | CFU Number |
|---|---|
| 1 | 77 |
| 2 | 69 |
| 3 | 66 |

Example 2—Device for Direct-Transfer of Arrayed Pattern of Bacterial Cells to Agar Media

*Staphylococcus aureus* (ATCC® 6538™) can be grown in nutrient broth for 48 hours at 35° C. The culture can be diluted 1.0E-4 into the coating solution. The coating solution may contain ascorbic acid (1% w/v), sucrose (2% w/v, Aldon Corporation IS28231), 1× phosphate buffered saline (PBS) in DI water. This solution can be sterilized and the *S. aureus* cells can be diluted into it in order to target between 1 and 20 cells per 100 nL volume.

The device can be thermoformed out of polypropylene plastic (40 mil, or 1 mm thick) into a device with dimensions 2.5" diameter×1" tall. The device can be sterilized by a number of know sterilization modalities.

The sterile device can then be coated with the prepared coating solution by dispensing 100 nL droplets onto the surface of the device in an array pattern (7×7 pattern for total of 49 drops) using an automated precision dispensing machine. The coated device is then allowed to air dry at room temperature until the $H_2O$ in the coating solution is substantially evaporated. The devices may then be placed into a moisture barrier package such as an aluminum mylar pouch or similar that also contains a desiccant and oxygen scavenger or a modified atmosphere.

The assembled device may be stored at 4° C., then removed from the packaging material at the point of use. The device can be directly contacted to the surface of trypticase soy agar (TSA) media in a petri dish so that the coated surface of the device is in contact with the surface of the agar media. The devices can be disposed and the inoculated TSA petri dish can be placed into a 35+/−2° C. incubator for approximately 18-24 hours. The CFUs can then be counted and are shown in Table 2.

TABLE 2

CFUs on TSA following contact with instant inoculator device with arrayed coating pattern (n = 3).

| Device # | CFUs |
|---|---|
| 1 | 49 |
| 2 | 50 |
| 3 | 49 |

Example 3—Device for Direct-Transfer of Bacterial Cells to Agar Media

*Bacillus subtilis* (ATCC® 6633™) was grown on trypticase soy agar (TSA) for 72 hours at 35° C. The spores were then harvested and purified. The coating solution was prepared by first adding synthetic broth powder to DI water (16.9 g/L) followed by steam sterilization of the media. Sucrose was then added to the synthetic broth and dissolved to yield 1% w/v. Then Triton X-100 was added to the solution to yield 0.04% Triton X-100. Finally, ascorbic acid was added to the solution to yield 0.1% w/v. This solution was then filter sterilized and the *B. subtilis* spores were diluted into it in order to target <100 CFU/100 µL volume.

The devices were injection molded out of polypropylene. Each device included 40 five mm diameter projections on the transfer region. The transfer region was about 2.25 inches in diameter and the handle region was about 1 inch tall. The devices were steam sterilized prior to coating.

The prepared coating solution was then dispensed (2.5 µL/projection) onto the surface of the sterilized device. The coated devices were then dried at room temperature for approximately 20 minutes or until the water in the coating solution was substantially evaporated. Sterile polypropylene caps were then placed over the transfer region of the coated devices. The devices (4 per pouch) were then placed into an aluminum mylar pouch that contained a desiccant and an oxygen scavenger. The pouch was then sealed with a heat sealer.

The sealed pouches were held at room temperature for approximately 1 hour in order to let the devices equilibrate to the package atmosphere. The pouch was then opened and a portion of the devices (n=2) were then removed from the packaging material. These devices were considered the 'time zero' pull point and were directly contacted to the surface of trypticase soy agar (TSA) media in a petri dish so that the coated surface of the device was in contact with the surface of the agar media. The device was contacted to the TSA surface for approximately 10 seconds, with a spreading motion, to allow *B. subtilis* to transfer from the surface of the device to the surface of the agar. The devices were then disposed and the inoculated TSA petri dish was placed into a 35° C. incubator for approximately 18 hours. The colony counts are shown in Table 3. The remaining devices in the pouch were immediately sealed and the package was placed at 35° C. for an accelerated aging study. After 2 days of storage at 35° C. (representative of 4-6 months at 4° C.) were removed from the package and directly contacted to the agar and incubated as was described for the time zero pull point. The CFU results are shown in Table 3.

TABLE 3

CFUs after direct transfer from device.

| Device # | T = 0 Pull | Pull 1 (following storage at 35° C. for 2 days) |
|---|---|---|
| 1 | 81 | 91 |
| 2 | 81 | 94 |

Example 4—Device for Direct-Transfer of Bacterial Cells to a Sample Collection Sponge Quantitative positive control devices for environmental monitoring sampling sponges and procedures were prepared in the following way: *Escherichia coli* (ATCC® 8739™) was grown in synthetic broth for approximately 24 hours at 35° C. *E. coli* cells were diluted into a sterile coating solution containing sucrose (0.4% w/v), ascorbic acid (0.5%), casamino acids (0.6%), and triton X100 (0.04%) to yield approximately $5.0 \times 10^3$ CFU/device.

Devices for direct-transfer of bacterial cells to a sample collection sponge were injection molded out of polypropylene. Each device included forty, five mm diameter projections on the transfer region. The transfer region was about 2.25 inches in diameter and the handle region was about 1 inch tall. The devices and caps for the device were steam sterilized prior to coating.

The coating solution containing the *E. coli* cells was then dispensed (2.5 μL/projection, total coating volume of 100 μL) onto the surface of the sterilized device. The coated devices were then vacuum dried for approximately 20 with a final pressure of approximately 500 mTorr. Sterile polypropylene caps were then placed over the transfer region of the coated devices. The devices were then placed into an aluminum mylar pouch that contained a desiccant and an oxygen scavenger. The pouch was then sealed with a heat sealer and stored at 2-8° C.

On the day of testing, the pouches were removed from 2-8° C. storage and placed at ambient conditions for 15 minutes. The coated devices were then removed from the pouches. The target in this study was World Bioproducts sponges (SAM-EZ-10NB-PUR) and 3M sponges (HS10NB). Both of these sponges come pre-wetted with neutralizing buffer from the respective manufacturer, and were directly contacted, in accordance with their IFU's, with the coated transfer region of the prepared positive control devices. The sponges were then placed into the plastic bags they came in and the neutralizing buffer was squeezed out of the sponges to recover the microbes. The recovery solution was then sampled and plated onto TSA. The TSA plates were incubated at 35° C. for 24 hours. The CFU results recovered from the sponges are shown in Table 4, the total volume of liquid recovered from each sponge was used to calculate the CFU/device. In addition, a control set of devices were sampled directed by submerging the transfer region in 10 mL of phosphate buffered saline in a sterile petri dish. A sample of this recovery buffer was then plated on TSA to determine the number of viable cells per device. Average viable CFU for the control devices was determined to be $4.9 \times 10^3$ CFU/device. This number was used to determine the percentage recovery for each sponge type.

TABLE 4

CFUs after direct transfer from device.

| | CFU/device | | % Recovery | |
|---|---|---|---|---|
| | WB | 3M | WB | 3M |
| 1 | 1.17E+03 | 2.42E+03 | 24% | 49% |
| 3 | 1.03E+03 | 1.78E+03 | 21% | 36% |
| 4 | 2.05E+03 | 1.33E+03 | 42% | 27% |
| 5 | 1.28E+03 | 1.04E+03 | 26% | 21% |
| 6 | 1.30E+03 | 1.78E+03 | 27% | 36% |
| Average | 1.37E+03 | 1.67E+03 | 28% | 34% |

Example 5—Device for Direct-Transfer of Bacterial Cells to a Liquid Target

*Staphylococcus aureus* (ATCC® 6538™) can be grown in nutrient broth for 48 hours at 35° C. The culture can be diluted into the coating solution. The coating solution may contain synthetic broth (HiMedia M334-500G), sucrose (1% w/v, Aldon Corporation IS28231), and Triton X-100 (0.04% v/v, Electron Microscopy Sciences 22140) in DI water. This solution may be filter sterilized and the *S. aureus* cells can be diluted into the coating solution in order to target <100 CFU/5 μL volume.

Device for direct-transfer of bacterial cells to a liquid target were prepared by cutting 8 inch sections of polypropylene rod (¼" outside diameter) and placing a 1.5" section of silicone tubing at one end of the rod to create a handle region. Hollow polypropylene tubing (¼" inside diameter) was then cut to approximately 7" to be used as the cap or sleeve that protects the coated end of the rod. The assembled devices can then be steam sterilized at 121° C. for 20 minutes.

The prepared coating solution can then be dispensed (5 μL) onto the end of the rod opposite to the handle region. The coated devices can then be vacuum dried for approximately 20 minutes with a final pressure of approximately 500 mTorr. The devices can then be capped using a hollow tube to protect the coated transfer region. The assembled device may then be placed into a moisture barrier package such as an aluminum mylar pouch that also contains a desiccant and oxygen scavenger and stored at 2-8° C. until use.

The assembled devices may then be removed from the packaging material at the time of use. The devices can then be used to directly inoculate 10 mL of trypticase soy broth (TSB) by contacting the coated transfer region of the rod with the TSB and shaking the rod briefly to allow the viable cells to transfer to the broth. The devices can then be disposed into biohazardous waste stream and the inoculated TSB can be incubated at 35° C. for approximately 24 hours. The presence of turbidity in the TSB tubes can indicate that the TSB to be qualified can support low levels of microbial inoculums (<100 CFU). A negative control can be run as well to ensure that the TSB was not contaminated prior to inoculation. The expected results are shown in Table 5.

TABLE 5

Presence or absence of turbidity (+/−) in inoculated TSB tubes.

| Device # | Turbidity (+/−) |
|---|---|
| 1 | + |
| 2 | + |
| 3 | + |
| Negative Control | − |

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An inoculating system, comprising:
    an inoculating member having a transfer region, a handle region, and a cap receiving region;
    a coating solution comprising 1 to 1000 colony forming units of viable microorganisms and a stabilizing agent coated and dried on a surface of the transfer region;
    a cap removably disposed over the transfer region that is secured to the inoculating member in the cap receiving region;
    wherein the inoculating member and cap are further sealed in a moisture barrier container;
    wherein the viable microorganisms are stable in the sealed moisture barrier container for at least 90 days;
    wherein the viable microorganisms define an inoculum;
    wherein the inoculating member is configured to transfer the viable microorganisms to a solid target or a liquid solution target from the inoculating member in a dry state without the need for an additional step to prepare the inoculum; and
    wherein the viable microorganisms are substantially transferred to the solid target or the liquid solution target in 30 seconds or less.
2. The inoculating system of claim 1, wherein the transfer region includes a rounded peripheral surface.
3. The inoculating system of claim 1, wherein the transfer region is configured to transfer 50% or more of the viable microorganisms to the target.
4. The inoculating system of claim 1, wherein the target has a water content of 5% or more.
5. The inoculating system of claim 1, wherein the target includes agar media.
6. The inoculating system of claim 1, wherein the target includes a liquid.
7. The inoculating system of claim 1, wherein the target includes a microbial collection device.
8. The inoculating system of claim 1, wherein a plurality of projections are disposed along the transfer region.
9. The inoculating system of claim 8, wherein the viable microorganisms are disposed on one or more of the projections.
10. The inoculating system of claim 9, wherein one or more of the projections include a convex surface.
11. The inoculating system of claim 10 wherein the transfer region includes 2 to 100 projections that each have a diameter of 1 mm to 5 mm.
12. The inoculating system of claim 1, wherein the viable microorganisms are stable in the moisture barrier container for at least 180 days.
13. The inoculating system of claim 1, wherein the moisture barrier container has a modified atmosphere.
14. The inoculating system of claim 1, wherein the moisture barrier container comprises a desiccant.
15. The inoculating system of claim 1, wherein the viable microorganisms are substantially transferred to the solid target or the liquid solution target in 10 seconds or less.
16. The inoculating system of claim 1, wherein at least 90% of the viable microorganisms are substantially transferred to the solid target or the liquid solution target in 30 seconds or less.
17. The inoculating system of claim 1, wherein at least 90% of the viable microorganisms are substantially transferred to the solid target or the liquid solution target in 10 seconds or less.
18. The inoculating system of claim 1, wherein the cap receiving region includes one or more spacers that are configured to allow air flow into the cap.
19. The inoculating system of claim 1, wherein the stabilizing agent includes one or more of a sugar, a polyol, a polymer, an antioxidant, an amino acid, a surfactant, and a buffer.
20. The inoculating system of claim 1, wherein the coating solution comprises an antioxidant and a surfactant.
21. The inoculating system of claim 1, wherein the inoculating member comprises an elongated rod.
22. The inoculating system of claim 1, wherein the handle region comprises an elongated rod.
23. The inoculating system of claim 1, wherein the transfer region has a surface area between 0.75 mm$^2$ and 300 mm$^2$.
24. The inoculating system of claim 1, wherein the transfer region has a surface area between 4 mm$^2$ and 100 mm$^2$.
25. The inoculating system of claim 1, wherein the transfer region includes a convex surface.
26. The inoculating system of claim 1, wherein the transfer region includes a planar surface.
27. The inoculating system of claim 1, wherein the viable microorganisms are stable on the transfer region for at least 180 days when stored at a temperature of 20 degrees Celsius or less.

28. An inoculating system, comprising:
- an inoculating member having a transfer region, a handle region, and a cap receiving region;
- a coating solution comprising viable microorganisms and a stabilizing agent coated and dried on a surface of the transfer region;
- a cap removably disposed over the transfer region that is secured to the inoculating member in the cap receiving region;
- wherein the inoculating member and cap are further sealed in a moisture barrier container;
- wherein the viable microorganisms are stable in the sealed moisture barrier container for at least 90 days;
- wherein the viable microorganisms define an inoculum;
- wherein the inoculating member is configured to transfer the viable microorganisms to a solid target or a liquid solution target from the inoculating member in a dry state without the need for an additional step to prepare the inoculum; and
- wherein the viable microorganisms are substantially transferred to the solid target or the liquid solution target in 30 seconds or less.

\* \* \* \* \*